United States Patent
Bosmans et al.

(10) Patent No.: US 6,544,997 B1
(45) Date of Patent: Apr. 8, 2003

(54) 4-(AMINOMETHYL)-PIPERIDINE BENZAMIDES FOR TREATING GASTROINTESTINAL DISORDERS

(75) Inventors: Jean-Paul René Marie André Bosmans, Rijkevorsel; Ann Louise Gabriëlle Meulemans, Mol; Michel Anna Jozef De Cleyn, Mekrplas, all of (BE); Henricus Jacobus Maria Gijsen, Breda (NL)

(73) Assignee: Janssen Pharmaceutica, N.V. (BE)

( * ) Notice: Subject to any disclaimer, the term of this patent is extended or adjusted under 35 U.S.C. 154(b) by 0 days.

(21) Appl. No.: 09/857,905

(22) PCT Filed: Dec. 14, 1999

(86) PCT No.: PCT/EP99/10064

§ 371 (c)(1), (2), (4) Date: Jun. 8, 2001

(87) PCT Pub. No.: WO00/37461

PCT Pub. Date: Jun. 29, 2000

(30) Foreign Application Priority Data

Dec. 22, 1998 (EP) .............................. 98204411

(51) Int. Cl.$^7$ ..................... C07D 405/12; C07D 405/14; C07D 513/04; A61K 31/445; A61P 1/100
(52) U.S. Cl. .................. 514/255.05; 546/196; 546/197; 546/199; 514/320; 514/322; 514/275; 544/407; 544/320
(58) Field of Search .................. 546/196, 197, 546/199; 514/320, 322, 255.05, 275; 544/407, 320

(56) References Cited

FOREIGN PATENT DOCUMENTS

| EP | 0 389 037 A1 | 9/1990 |
|---|---|---|
| WO | 0389037 * | 3/1990 |
| WO | WO 93/05038 A1 | 3/1993 |
| WO | WO 93/16072 A1 | 8/1993 |
| WO | WO 94/10174 A1 | 5/1994 |

* cited by examiner

Primary Examiner—Mukund J. Shah
Assistant Examiner—Hong Liu

(57) ABSTRACT

The present invention of compounds of formula (I)

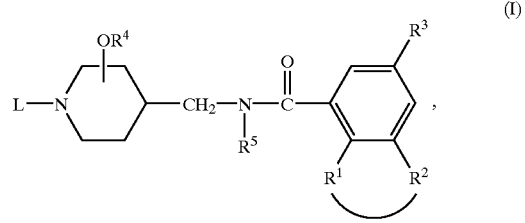

a stereochemically isomeric form thereof, an N-oxide form thereof or a pharmaceutically acceptable acid addition salt thereof, —$R^1$—$R^2$— is a bivalent radical of formula wherein in said bivalent radicals one or two hydrogen atoms may be substituted with $C_{1-6}$alkyl or hydroxy; $R^3$ is hydrogen or halo; $R^4$ is hydrogen or $C_{1-6}$alkyl; $R^5$ is hydrogen or $C_{1-6}$alkyl; L is $C_{3-6}$cycloalkyl, oxo$C_{5-6}$cycloalkyl, $C_{2-6}$alkenyl, or L is a radical of formula —Alk—$R^6$—, Alk—X—$R^7$, —Alk—Y—C(=O)—$R^9$, or —Alk—Y—C(=O)—$NR^{11}R^{12}$ wherein each Alk is $C_{1-12}$alkanediyl; and $R^6$ is hydrogen, amino, cyano, $C_{1-6}$alkylsulfonylamino, $C_{3-6}$cycloalkyl, oxo$C_{5-6}$cycloalkyl, aryl or a heterocyclic ringsystem; $R^7$ is hydrogen, $C_{1-6}$alkyl, hydroxy$C_{1-6}$alkyl, $C_{3-6}$cycloalkyl, aryl or a heterocyclic ringsystem; X is O, S, $SO_2$ or $NR^8$; said $R^8$ being hydrogen or $C_{1-6}$alkyl; $R^9$ is hydrogen, $C_{1-6}$alkyl, $C_{3-6}$cycloalkyl, $C_{1-6}$alkyloxy, hydroxy or aryl; Y is a direct bond or $NR^{10}$; said $R^{10}$ being hydrogen, or $C_{1-6}$alkyl; $R^{11}$ and $R^{12}$ each independently are hydrogen, $C_{1-6}$alkyl, $C_{3-6}$cycloalkyl, or $R^{11}$ and $R^{12}$ combined with the nitrogen atom may form an optionally substituted pyrrolidinyl, piperidinyl, piperazinyl or 4-morpholinyl ring. Processes for preparing said products, formulations comprising said products and their use as a medicine are disclosed, in particular for treating or preventing gastrointestinal disorders.

9 Claims, No Drawings

4-(AMINOMETHYL)-PIPERIDINE BENZAMIDES FOR TREATING GASTROINTESTINAL DISORDERS

CROSS REFERENCE TO RELATED APPLICATIONS

This application is the national stage of Application No. PCT/EP99/10064, filed Dec. 14, 1999 which application claims priority from EP 98204411.7, filed Dec. 22, 1998.

The present invention is concerned with novel compounds of formula (I) having favourable gastrointestinal properties. The invention further relates to methods for preparing such novel compounds, pharmaceutical compositions comprising said novel compounds as well as the use as a medicine of said compounds.

WO 93/05038, published on Mar. 18, 1993 (SmithKline Beecham PLC) discloses a number of substituted 4-piperidinylmethyl 8-amino-7-chloro-1,4-benzodioxan-5-carboxamides having $5HT_4$-receptor antagonistic activity.

WO 94/10174, published on May 11, 1994 (SmithKline Beecham PLC) discloses a number of substituted 4-pyridinylmethyl oxazino[3,2-a]indole-carboxamide derivatives having $5HT_4$-receptor antagonistic activity.

WO 93/16072, published on Aug. 19, 1993 discloses N-[(1-butyl-4-piperidinyl)-methyl]-6-chloro-3,4-dihydro-2H-1-benzopyran-8-carboxamide having $5\ HT_4$ receptor antagonistic activity.

The compounds of the present invention differ from the cited art-known compounds structurally, by the presence of a hydroxy or a $C_{1-6}$alkyloxygroup on the 3- or 4-position of the piperidine moiety, by the presence of a methylene group between the carbamoyl group and the piperidine ring, and by the absence of an amino group on the 4-position of the benzamide moiety.

Unexpectedly, the present compounds of formula (I) have favourable gastrointestinal properties.

The present invention concerns a compound of formula (I)

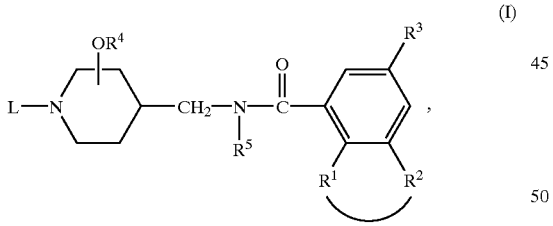

a stereochemically isomeric form thereof, an N-oxide form thereof, a prodrug thereof, or a pharmaceutically acceptable acid or base addition salt thereof,
wherein
—$R^1$—$R^2$— is a bivalent radical of formula —O—CH$_2$—O— , (a-1)

—O—CH$_2$—CH$_2$— , (a-2)

—O—CH$_2$—CH$_2$—O— , (a-3)

—O—CH$_2$—CH$_2$—CH$_2$— , (a-4)

—O—CH$_2$—CH$_2$—CH$_2$—O— , (a-5)

—O—CH$_2$—CH$_2$—CH$_2$—CH$_2$— , (a-6)

—O—CH$_2$—CH$_2$—CH$_2$—CH$_2$—O— , (a-7)

—O—CH$_2$—CH$_2$—CH$_2$—CH$_2$—CH$_2$— , (a-8)

wherein in said bivalent radicals optionally one or two hydrogen atoms on the same or a different carbon atom may be replaced by $C_{1-6}$alkyl or hydroxy, $R^3$ is hydrogen or halo;
$R^4$ is hydrogen or $C_{1-6}$alkyl;
$R^5$ is hydrogen or $C_{1-6}$alkyl;
L is $C_{3-6}$cycloalkyl, oxo$C_{5-6}$cycloalkyl, or $C_{2-6}$alkenyl, or L is a radical of formula —Alk—$R^6$, (b-1)

—Alk—X—$R^7$, (b-2)

—Alk—Y—C(=O)—$R^9$, or (b-3)

—Alk—Y—C(=O)—NR$^{11}$R$^{12}$, (b-4)

wherein each Alk is $C_{1-12}$alkanediyl; and
$R^6$ is hydrogen, cyano, amino, $C_{1-6}$alkylsulfonylamino, $C_{3-6}$cycloalkyl, oxo$C_{5-6}$cycloalkyl, aryl or Het$^1$;
$R^7$ is hydrogen, $C_{1-6}$alkyl, hydroxy$C_{1-6}$alkyl, $C_{3-6}$cycloalkyl, aryl or Het$^2$;
X is O, S, SO$_2$ or NR$^8$; said $R^8$ being hydrogen or $C_{1-6}$alkyl;
$R^9$ is hydrogen, $C_{1-6}$alkyl, $C_{3-6}$cycloalkyl, $C_{1-6}$alkyloxy, hydroxy or aryl;
Y is a direct bond, NR$^{10}$, O, S, O—(CH$_2$)$_n$—, S—(CH$_2$)$_n$—, or —NR$^{10}$—(CH$_2$)$_n$—, wherein n is an integer from 1 to 6, and $R^{10}$ being hydrogen or $C_{1-6}$alkyl;
$R^{11}$ and $R^{12}$ each independently are hydrogen, $C_{1-6}$alkyl, $C_{3-6}$cycloalkyl, or $R^{11}$ and $R^{12}$ combined with the nitrogen atom bearing $R^{11}$ and $R^{12}$ may form a pyrrolidinyl or piperidinyl ring both being optionally substituted with $C_{1-6}$alkyl, amino or mono or di($C_{1-6}$alkyl)amino, or said $R^{11}$ and $R^{12}$ combined with the nitrogen bearing $R^{11}$ and $R^{12}$ may form a piperazinyl or 4-morpholinyl radical both being optionally substituted with $C_{1-6}$alkyl; and
each aryl represents unsubstituted phenyl or phenyl substituted with 1, 2 or 3 substituents each independently selected from halo, hydroxy, $C_{1-6}$alkyl, $C_{1-6}$alkyloxy, amino-sulfonyl, $C_{1-6}$alkylcarbonyl, nitro, trifluoromethyl, amino or aminocarbonyl; and
Het$^1$ and Het$^2$ each independently are selected from furan; furan substituted with $C_{1-6}$alkyl or halo; tetrahydrofuran; tetrahydrofuran substituted with $C_{1-6}$alkyl; dioxolane; dioxolane substituted with $C_{1-6}$alkyl; dioxane; dioxane substituted with $C_{1-6}$alkyl; tetrahydropyran; tetrahydropyran substituted with $C_{1-6}$alkyl; pyrrolidinyl; pyrrolidinyl substituted with one or two substituents each independently selected from halo, hydroxy, cyano, or $C_{1-6}$alkyl; pyridinyl; pyridinyl substituted with one or two substituents each independently selected from halo, hydroxy, cyano, $C_{1-6}$alkyl; pyrimidinyl; pyrimidinyl substituted with one or two substituents each independently selected from halo, hydroxy, cyano, $C_{1-6}$alkyl, $C_{1-6}$alkyloxy, amino and mono and di($C_{1-6}$alkyl)amino; pyridazinyl; pyridazinyl substituted with one or two substituents each independently selected from hydroxy, $C_{1-6}$alkyloxy, $C_{1-6}$alkyl or halo; pyrazinyl; pyrazinyl substituted with one ore two substituents each independently selected from halo, hydroxy, cyano, $C_{1-6}$alkyl, $C_{1-6}$alkyloxy, amino, mono- and di($C_{1-6}$alkyl)amino and $C_{1-6}$alkyloxycarbonyl;

$Het^1$ can also be a radical of formula

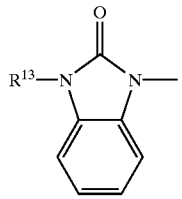
(c-1)

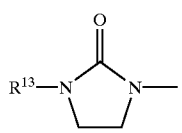
(c-2)

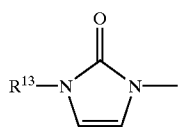
(c-3)

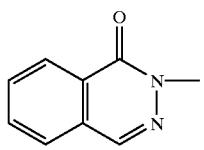
(c-4)

$Het^1$ and $Het^2$ each independently can also be selected from the radicals of formula

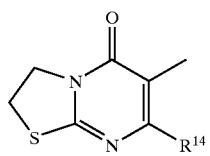
(d-1)

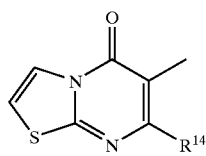
(d-2)

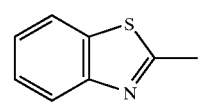
(d-3)

$R^{13}$ and $R^{14}$ each independently are hydrogen or $C_{1-4}$alkyl.

As used in the foregoing definitions halo is generic to fluoro, chloro, bromo and iodo; $C_1$4alkyl defines straight and branched chain saturated hydrocarbon radicals having from 1 to 4 carbon atoms such as, for example, methyl, ethyl, propyl, butyl, 1-methyl-ethyl, 2-methylpropyl and the like; $C_{1-6}$alkyl is meant to include $C_{1-4}$alkyl and the higher homologues thereof having 5 or 6 carbon atoms, such as, for example, 2-methyl-butyl, pentyl, hexyl and the like; $C_{3-6}$cycloalkyl is generic to cyclopropyl, cyclobutyl, cyclopentyl and cyclohexyl; $C_{2-6}$alkenyl defines straight and branched chain unsaturated hydrocarbon radicals having from 2 to 6 carbon atoms, such as ethenyl, propenyl, butenyl, pentenyl or hexenyl; $C_{1-12}$alkanediyl defines bivalent straight or branched chain hydrocarbon radicals containing from 1 to 12 carbon atoms such as, for example, 1,2-ethanediyl, 1,3-propanediyl, 1,4-butanediyl, 1,5-pentanediyl, 1,6-hexanediyl, 1,7-heptanediyl, 1,8-octanediyl, 1,9-nonanediyl, 1,10-decanediyl, 1,11-undecanediyl, 1,12-dodecanediyl and the branched isomers thereof. $C_{1-6}$alkanediyl is defined in an analogous way as $C_{1-12}$alkanediyl.

The $—OR^4$ radical is preferably situated at the 3- or 4-position of the piperidine moiety.

The term "stereochemically isomeric forms" as used hereinbefore defines all the possible isomeric forms which the compounds of formula (I) may possess. Unless otherwise mentioned or indicated, the chemical designation of compounds denotes the mixture of all possible stereochemically isomeric forms, said mixtures containing all diastereomers and enantiomers of the basic molecular structure. More in particular, stereogenic centers may have the R- or S-configuration; substituents on bivalent cyclic (partially) saturated radicals may have either the cis- or trans-configuration. Compounds encompassing double bonds can have an E or Z-stereochemistry at said double bond. Stereochemically isomeric forms of the compounds of formula (I) are obviously intended to be embraced within the scope of this invention.

The term prodrug as used throughout this text means the pharmacologically acceptable derivatives, e.g. esters and amides, such that the resulting biotransformation product of the derivative is the active drug as defined in the compounds of formula (I). The reference by Goodman and Gilman (The Pharmacological Basis of Therapeutics, $8^{th}$ ed., McGraw-Hill, Int. Ed. 1992, "Biotransformation of Drugs", p. 13–15) describing prodrugs generally, is hereby incorporated.

The pharmaceutically acceptable acid and base addition salts as mentioned hereinabove are meant to comprise the therapeutically active non-toxic acid and base addition salt forms which the compounds of formula (I) are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butane-dioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

Conversely said salt forms can be converted by treatment with an appropriate base into the free base form.

The compounds of formula (I) containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term addition salt as used hereinabove also comprises the solvates which the compounds of formula (I) as well as the salts thereof, are able to form. Such solvates are for example hydrates, alcoholates and the like.

Some of the compounds of formula (I) may also exist in their tautomeric form. Such forms although not explicitly indicated in the above formula are intended to be included within the scope of the present invention. For instance, when an aromatic heterocyclic ring is substituted with hydroxy the keto-form may be the mainly populated tautomer.

The N-oxide forms of the compounds of formula (I), which may be prepared in art-known manners, are meant to comprise those compounds of formula (I) wherein one or several nitrogen atoms are oxidized to the N-oxide. Particularly those N-oxides are envisaged wherein the piperidine-nitrogen is N-oxidized.

A first group of interesting compounds are compounds of formula (I), stereochemically isomeric forms thereof, N-oxide forms thereof, or pharmaceutically acceptable acid or base addition salts thereof, wherein
—$R^1$—$R^2$— is a bivalent radical of formula —O—$CH_2$—O—,                           (a-1)

—O—$CH_2$—$CH_2$—,                      (a-2)

—O—$CH_2$—$CH_2$—O—,                   (a-3)

—O—$CH_2$—$CH_2$—$CH_2$—,              (a-4)

—O—$CH_2$—$CH_2$—$CH_2$—O—,            (a-5)

—O—$CH_2$—$CH_2$—$CH_2$—$CH_2$—,       (a-6)

—O—$CH_2$—$CH_2$—$CH_2$—$CH_2$—O—,     (a-7)

—O—$CH_2$—$CH_2$—$CH_2$—$CH_2$—$CH_2$—, (a-8)

wherein in said bivalent radicals optionally one or two hydrogen atoms on the same or a different carbon atom may be replaced by $C_{1-6}$alkyl or hydroxy, $R^3$ is hydrogen or halo;
$R^4$ is hydrogen or $C_{1-6}$alkyl;
$R^5$ is hydrogen or $C_{1-6}$alkyl;
L is $C_{3-6}$cycloalkyl, oxo$C_{5-6}$cycloalkyl, or $C_{2-6}$alkenyl, or L is a radical of formula —Alk—$R^6$,                              (b-1)

—Alk—X—$R^7$,                            (b-2)

—Alk—Y—C(=O)—$R^9$, or                   (b-3)

—Alk—Y—C(=O)—$NR^{11}R^{12}$,            (b-4)

wherein each Alk is $C_{1-12}$alkanediyl; and
$R^6$ is hydrogen, hydroxy, cyano, amino, $C_{1-6}$alkylsulfonylamino, $C_{3-6}$cycloalkyl, oxo$C_5s_6$cycloalkyl, aryl or Het$^1$;
$R^7$ is hydrogen, $C_{1-6}$alkyl, hydroxy$C_{1-6}$alkyl, $C_{3-6}$cycloalkyl, aryl or Het$^2$;
X is O, S, $SO_2$ or $NR^8$; said $R^8$ being hydrogen or $C_{1-6}$alkyl;

$R^9$ is hydrogen, $C_{1-6}$alkyl, $C_{3-6}$cycloalkyl, $C_{1-6}$alkyloxy, hydroxy or aryl;
Y is a direct bond or $NR^{10}$; said $R^{10}$ being hydrogen or $C_{1-6}$alkyl;
$R^{11}$ and $R^{12}$ each independently are hydrogen, $C_{1-6}$alkyl, $C_{3-6}$cycloalkyl, or R11 and $R^{12}$ combined with the nitrogen atom bearing $R^{11}$ and $R^{12}$ may form a pyrrolidinyl or piperidinyl ring both being optionally substituted with $C_{1-6}$alkyl, amino or mono or di($C_{1-6}$alkyl)amino, or said $R^{11}$ and $R^{12}$ combined with the nitrogen bearing $R^{11}$ and $R^{12}$ may form a piperazinyl or 4-morpholinyl radical both being optionally substituted with $C_{1-6}$alkyl; and each aryl represents unsubstituted phenyl or phenyl substituted with 1, 2 or 3 substituents each independently selected from halo, hydroxy, $C_{1-6}$alkyl, $C_{1-6}$alkyloxy, amino-sulfonyl, $C_{1-6}$alkylcarbonyl, nitro, trifluoromethyl, amino or aminocarbonyl; and Het$^1$ and Het$^2$ each independently are selected from furan; furan substituted with $C_{1-6}$alkyl or halo; tetrahydrofuran; tetrahydrofuran substituted with $C_{1-6}$alkyl; dioxolane; dioxolane substituted with $C_{1-6}$alkyl; dioxane; dioxane substituted with $C_{1-6}$alkyl; tetrahydropyran; tetrahydropyran substituted with $C_{1-6}$alkyl; pyrrolidinyl; pyrrolidinyl substituted with one or two substituents each independently selected from halo, hydroxy, cyano, or $C_{1-6}$alkyl; pyridinyl; pyridinyl substituted with one or two substituents each independently selected from halo, hydroxy, cyano, $C_{1-6}$alkyl; pyrimidinyl; pyrimidinyl substituted with one or two substituents each independently selected from halo, hydroxy, cyano, $C_{1-6}$alkyl, $C_{1-6}$alkyloxy, amino and mono and di($C_{1-6}$alkyl)amino; pyridazinyl; pyridazinyl substituted with one or two substituents each independently selected from hydroxy, $C_{1-6}$alkyloxy, $C_{1-6}$alkyl or halo; pyrazinyl; pyrazinyl substituted with one ore two substituents each independently selected from halo, hydroxy, cyano, $C_{1-6}$alkyl, $C_{1-6}$alkyloxy, amino, mono- and di($C_{1-6}$alkyl)amino and $C_{1-6}$alkyloxycarbonyl;

Het$^1$ can also be a radical of formula

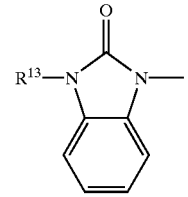

(c-1)

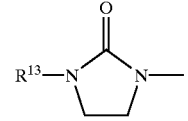

(c-2)

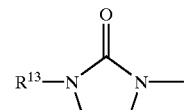

(c-3)

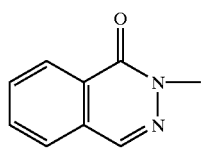
(c-4)

Het$^1$ and Het$^2$ each independently can also be selected from the radicals of formula

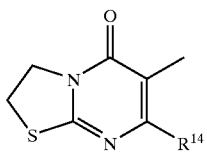
(d-1)

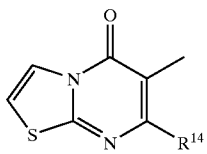
(d-2)

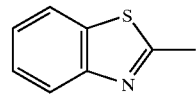
(d-3)

$R^{13}$ and $R^{14}$ each independently are hydrogen or $C_{1-4}$alkyl.

Another group of interesting compounds consists of those compounds of formula (I) wherein one or more of the following restrictions apply:

a) —$R^1$—$R^2$— is a radical of formula (a-1), (a-2), (a-3), (a4), (a-5), (a-6) or (a-7), wherein optionally one or two hydrogen atoms are substituted with $C_{1-4}$alkyl;
b) $R^3$ is fluoro, chloro or bromo; in particular chloro;
c) $R^4$ is hydrogen, methyl or ethyl, and the —$OR^4$ radical is situated at the 3- or 4-position of the piperidine ring; or
d) $R^5$ is hydrogen.

More interesting compounds are those compounds of formula (I) wherein the bivalent radical —$R^1$—$R^2$— is of formula (a-2), or (a-4), wherein in said bivalent radicals optionally one or two hydrogen atoms on the same or a different carbon atom are replaced by methyl.

Other more interesting compounds are those compounds of formula (I) wherein the bivalent radical —$R^1$—$R^2$— is of formula (a-3), (a-5), or (a-7), wherein in said bivalent radicals optionally one or two hydrogen atoms on the same or a different carbon atom are replaced by methyl.

Further more interesting compounds are those interesting compounds of formula (1) wherein $R^4$ is hydrogen or methyl.

Special compounds are those compounds of formula (I) wherein the radical L is of formula —Alk—$R^6$ (b-1) wherein $R^6$ is hydrogen, cyano or Het$^1$ and Het$^1$ is furan; furan substituted with $C_{1-6}$alkyl or halo; tetrahydrofuran; tetrahydrofuran substituted with $C_{1-6}$alkyl; dioxolane; dioxolane substituted with $C_{1-6}$alkyl; dioxane; dioxane substituted with $C_{1-6}$alkyl; tetrahydropyran; tetrahydropyran substituted with $C_{1-6}$alkyl. Other special compounds are those compounds of formula (I) wherein the radical L is of formula —Alk—X—$R^7$ (b-2) wherein X is O and $R^7$ is hydrogen, $C_{1-6}$alkyl or hydroxy$C_{1-4}$alkyl.

Yet other special compounds are those compounds of formula (I) wherein the radical L is of formula —Alk—Y—C(=O)—$R^9$ (b-3) wherein Y is a direct bond and $R^9$ is $C_{1-6}$alkyl, $C_{1-6}$alkyloxy, or hydroxy.

Particular compounds are those more interesting compounds wherein the —$OR^4$ radical, preferably representing hydroxy, is situated at the 3-position of the piperidine moiety having the trans configuration, i.e. the —$OR^4$ radical is in the trans position in relation to the methylene on the piperidine moiety.

Other particular compounds are those more interesting compounds wherein the —$OR^4$ radical is situated at the 4-position of the piperidine moiety.

Preferred compounds are those compounds of formula (I) wherein the bivalent radical —$R^1$—$R^2$— is a radical of formula (a-3) or (a-5), the —$OR^4$ radical is situated at the 3-position of the piperidine moiety having the trans configuration, and L is of formula —Alk—Y—C(=O)—$R^9$ (b-3) wherein Y is a direct bond and $R^9$ is $C_{1-6}$alkyloxy or hydroxy.

The compounds of the present invention can generally be prepared by N-alkylating an intermediate of formula (III) with an intermediate of formula (II), wherein W is an appropriate leaving group such as, for example, halo, e.g. fluoro, chloro, bromo, iodo, or in some instances W may also be a sulfonyloxy group, e.g. methanesulfonyloxy, benzenesulfonyloxy, trifluoromethanesulfonyloxy and the like reactive leaving groups. The reaction can be performed in a reaction-inert solvent such as, for example, acetonitrile, and optionally in the presence of a suitable base such as, for example, sodium carbonate, potassium carbonate or triethylamine. Stirring may enhance the rate of the reaction. The reaction may conveniently be carried out at a temperature ranging between room temperature and the reflux temperature of the reaction mixture.

L—W +
(II)

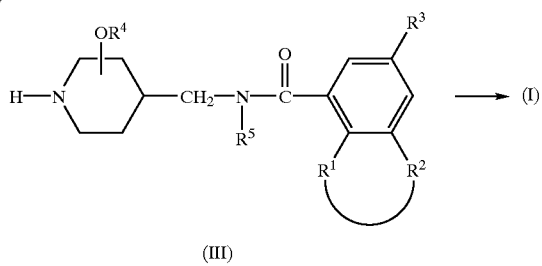

Alternatively, compounds of formula (I) can also be prepared by reductively N-alkylating an intermediate of formula (III) with an intermediate of formula L'=O (IV), wherein L'=O represents a derivative of formula L-H wherein two geminal hydrogen atoms are replaced by oxygen, following art-known reductive N-alkylation procedures.

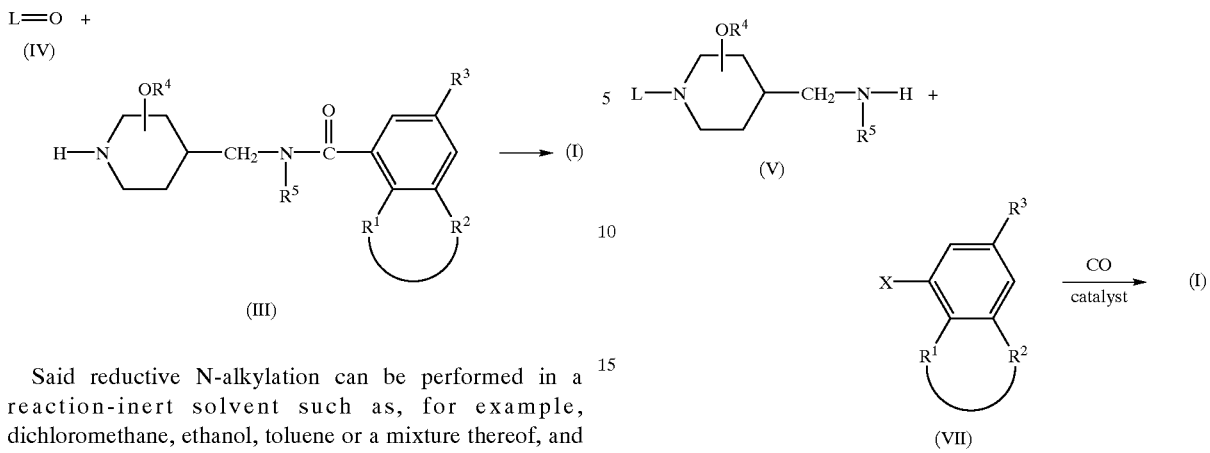

Said reductive N-alkylation can be performed in a reaction-inert solvent such as, for example, dichloromethane, ethanol, toluene or a mixture thereof, and in the presence of a reducing agent such as, for example, a borohydride, e.g. sodium borohydride, sodium cyanoborohydride or triacetoxy borohydride. It may also be convenient to use hydrogen as a reducing agent in combination with a suitable catalyst such as, for example, palladium-on-charcoal or platinum-on-charcoal. In case hydrogen is used as reducing agent, it may be advantageous to add a dehydrating agent to the reaction mixture such as, for example, aluminium tert-butoxide. In order to prevent the undesired further hydrogenation of certain functional groups in the reactants and the reaction products, it may also be advantageous to add an appropriate catalyst-poison to the reaction mixture, e.g., thiophene or quinoline-sulphur. To enhance the rate of the reaction, the temperature may be elevated in a range between room temperature and the reflux temperature of the reaction mixture and optionally the pressure of the hydrogen gas may be raised.

The compounds of formula (I) may be prepared by reacting an intermediate of formula (V) with an carboxylic acid derivative of formula (VI) or a reactive functional derivative thereof, such as, e.g. carbonyl imidazole derivatives or mixed anhydrides. Said amide-bond formation may be performed by stirring the reactants in an appropriate solvent, optionally in the presence of a base, such as sodium imidazolide or triethylamine.

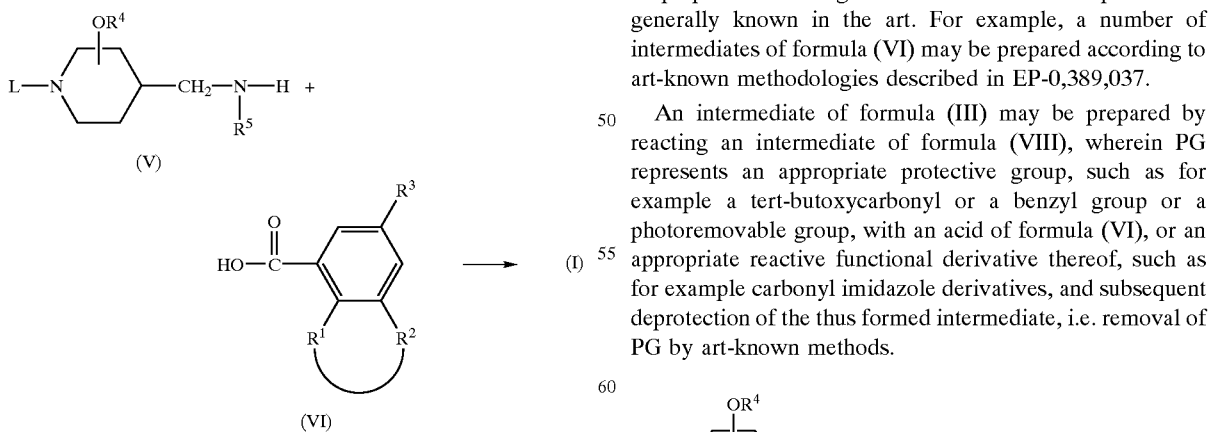

Further, compounds of formula (I) can be prepared by carbonylation of an intermediate of formula (VII), wherein X is bromo or iodo, in the presence of an intermediate of formula (V).

Said carbonylation reaction can be carried out in a reaction-inert solvent such as, e.g. acetonitrile or tetrahydrofuran, in the presence of a suitable catalyst and a suitable base such as a tertiary amine e.g. triethylamine, and at a temperature ranging between room temperature and the reflux temperature of the reaction mixture. Suitable catalysts are, for instance, palladium(triphenylphosphine) complexes. Carbon monoxide is administered at atmospheric pressure or at an increased pressure. Analogous carbonylation reactions are described in Chapter 8 of "Palladium reagents in organic syntheses", Academic Press Ltd., Benchtop Edition 1990, by Richard F. Heck; and the references cited therein.

The compounds of formula (I) may further be prepared by converting compounds of formula (I) into each other according to art-known group transformation reactions. For instance, in compounds of formula (I) wherein L is a radical of formula —Alk—$R^6$ and $R^6$ is cyano said cyano can be converted into amino using art-known hydrogenation procedures such as, e.g. hydrogenation using Raney nickel as a catalyst.

The starting materials and some of the intermediates are known compounds and are commercially available or may be prepared according to conventional reaction procedures generally known in the art. For example, a number of intermediates of formula (VI) may be prepared according to art-known methodologies described in EP-0,389,037.

An intermediate of formula (III) may be prepared by reacting an intermediate of formula (VIII), wherein PG represents an appropriate protective group, such as for example a tert-butoxycarbonyl or a benzyl group or a photoremovable group, with an acid of formula (VI), or an appropriate reactive functional derivative thereof, such as for example carbonyl imidazole derivatives, and subsequent deprotection of the thus formed intermediate, i.e. removal of PG by art-known methods.

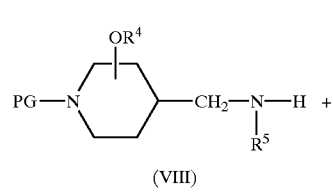

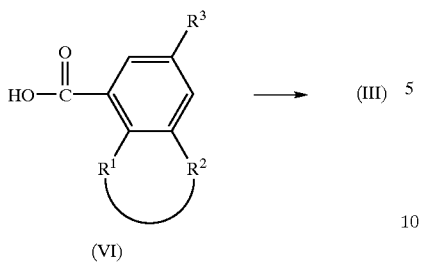

(VI)

An intermediate of formula (V) may be prepared by reacting an intermediate of formula (X), with an intermediate of formula (II). Said intermediate of formula (X) may be prepared by deprotection of an intermediate of formula (VIII).

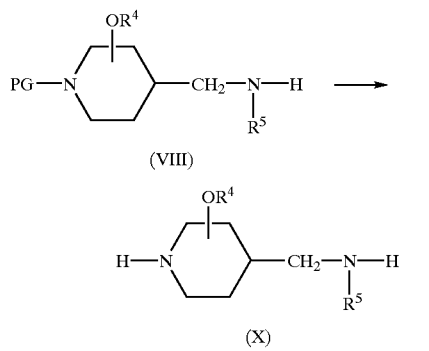

In some cases, it may be appropriate to protect the amine functionality bearing the $R^5$ radical in the above described reaction sequence. Protecting groups for amine functionalities are art-known. These protecting groups may then be removed at the appropriate time during the further synthesis.

Intermediates of formula (VIII-a), being intermediates of formula (VIII) wherein $PG^1$ is a protecting group which cannot be removed by hydrogenation such as e.g. a tert-butoxycarbonyl, can be prepared according to scheme 1.

Scheme 1

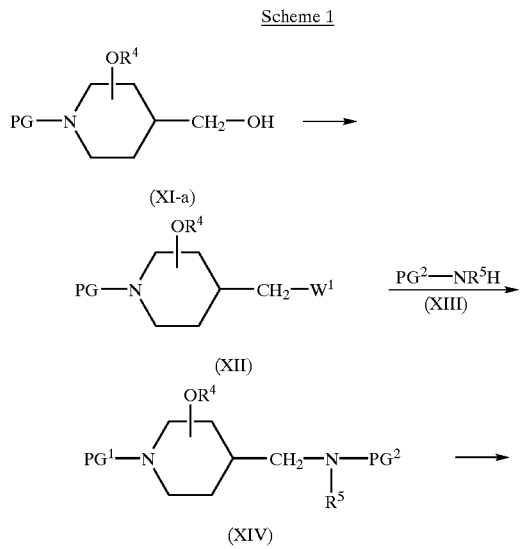

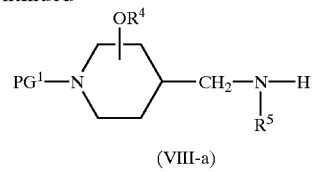

(VIII-a)

In scheme 1, an intermediate of formula (XI-a) is converted to an intermediate of formula (XII), wherein $W^1$ is a leaving group such as halo or sulfonyloxy. Subsequently, intermediate (XII) is treated with an intermediate of formula (XIII), wherein $PG^2$ is a protecting group which can be removed by hydrogenation such as, e.g. benzyl. Removal of the protecting group $PG^2$ from intermediate (XIV) yields intermediates of formula (VIII-a).

Intermediates of formula (VIII-a-1), defined as intermediates of formula (VIII-a) wherein $R^4$ is methyl, can be prepared as described in scheme 2.

Scheme 2

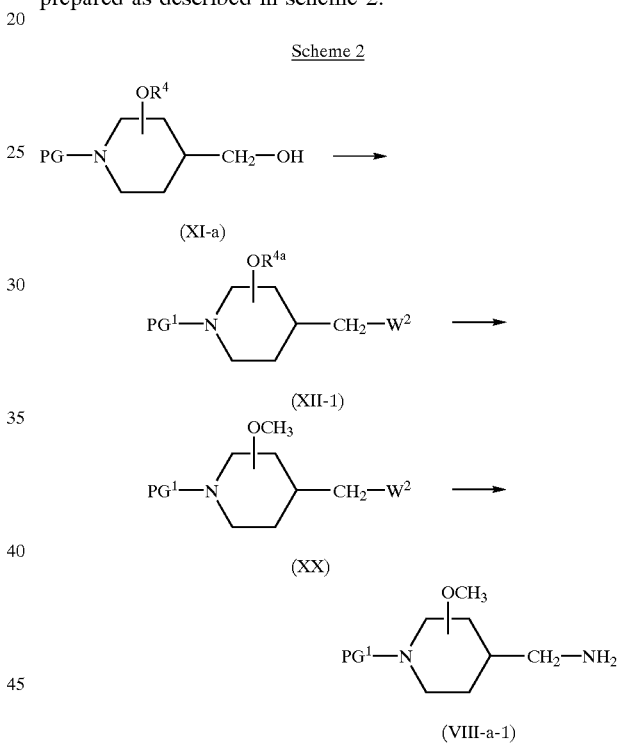

In scheme 2, an intermediate of formula (XI-a), wherein $R^{4a}$ is hydrogen, is converted to an intermediate of formula (XII-1), wherein $W^2$ is a suitable leaving group such as e.g. a tosylate group. Subsequently, the secundary hydroxy of intermediate (XII-1), i.e. the $—OR^{4a}$ moiety, is converted to a methoxy using suitable methylation conditions such as e.g. treatment with sodium hydride in tetrahydrofuran and addition of methyliodide. Conversion of intermediate (XX) to intermediate (VIII-a-1) can be done using art-known reaction procedures.

In an aspect of the present invention, novel compounds of formula (IX) are provided wherein $R^{15}$ and $R^{16}$ are each independently selected from hydrogen or a protective group PG, and $R^4$ and $R^5$ are as defined above. Suitable protecting groups PG are, e.g. $C_{1-4}$alkylcarbonyl, $C_{1-4}$alkyloxycarbonyl, trihalomethylcarbonyl, diphenylmethyl, triphenylmethyl or arylmethyl, wherein aryl is phenyl optionally substituted with up to two substituents selected from $C_{1-4}$alkyloxy or halo. Said novel compounds of formula (IX) comprise the intermediates of formula (VIII), (X) and (XIV).

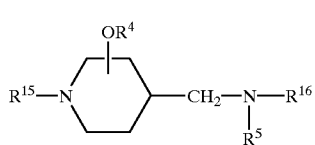

(IX)

Intermediates of formula (XI-a), wherein $PG^1$ is a protecting group which cannot be removed by hydrogenation such as e.g. a tert-butoxycarbonyl, can be converted to intermediates of formula (XI-b), wherein PG2 is a protecting group which can be removed by hydrogenation such as, e.g. benzyl, using an appropriate deprotection—protection reaction sequence. Conversely, intermediates of formula (Xl-b) can also be converted to intermediates of formula (XI-a).

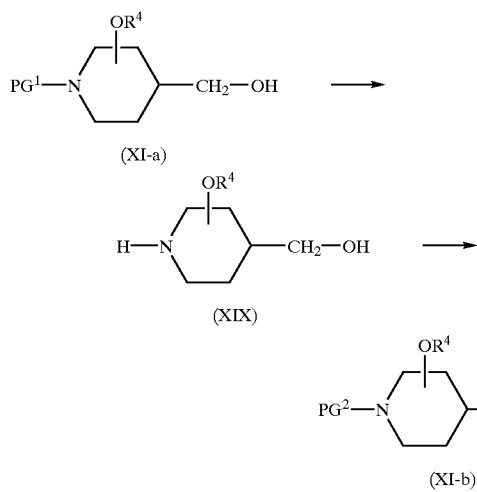

An intermediate of formula (XI-b), wherein the —$OR^4$ moiety is located on the 3-position of the piperidine moiety, $R^4$ is a hydrogen and $PG^2$ is a benzyl group, having the trans configuration, is known from *J. Med. Chem.* 16, pp. 156–159 (1973). Said article also describes an intermediate of formula (XIX), wherein the —$OR^4$ moiety is located on the 3-position of the piperidine moiety and $R^4$ is a hydrogen, having the trans configuration.

Intermediates of formula (XI-1-a) are defined as intermediates of formula (XI-a) wherein the —$OR^4$ moiety is located on the 3-position of the piperidine moiety.

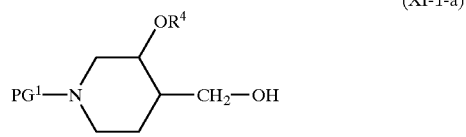

Those intermediates of formula (XI-1-a) wherein $R^4$ is $C_{1-6}$alkyl and having the cis configuration can be prepared by hydrogenating an intermediate of formula (XVI) following art-known methods. The intermediate (XVI), wherein $PG^1$ and PG2 are as defined above, can be prepared by reacting a protected piperidone of formula (XV) with a phosphonium reagent of formula [(aryl)$_3$P—$CH_2$—O—$PG^2$]$^+$-halide$^-$, in appropriate conditions for carrying out a Wittig-type reaction. Subsequent removal of $PG^2$ yields intermediates of formula (XI-1-a) having the cis configuration.

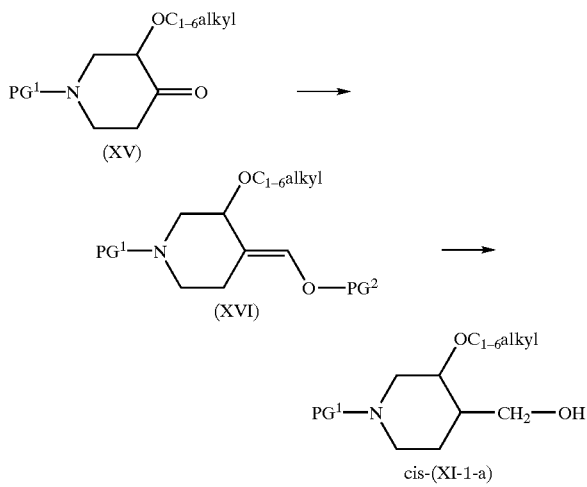

A way of preparing an intermediate of formula (X-1-b) having the trans-configuration was found. Said novel preparation starts from an intermediate of formula (XI-1-b) having the cis-configuration or from an intermediate of formula (XVII) having the cis-configuration. In said intermediates of formula (XI-1-b) and (XVII) $PG^2$ is as defined above, $R^{4a}$ is hydrogen, $C_{1-6}$alkyl or a protective group such as for example, benzyl, tert-butoxycarbonyl and the like.

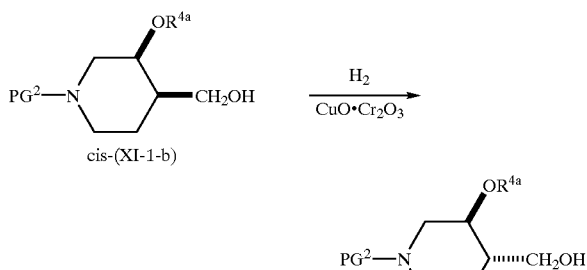

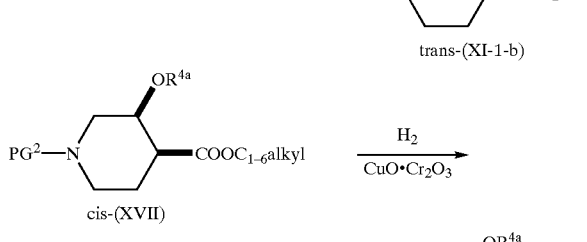

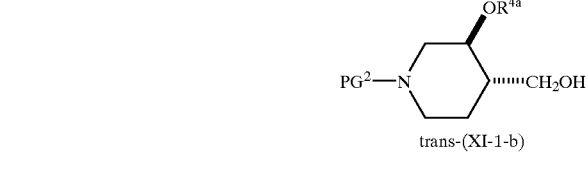

Said inversion-reaction is carried out in an appropriate solvent, such as, for example an ether, e.g. tetrahydrofuran in the presence of $CuO.Cr_2O_3$ under a hydrogen atmosphere and in the presence of an appropriate base, such as, for example calciumoxide.

The preferred hydrogen pressure and reaction temperature is dependent upon the starting material. Starting from cis-(XI-1-b) the hydrogen pressure preferably ranges from 900 to 2000 kPa (measured at room temperature) and the reaction temperature ranges from room temperature up to 200° C., preferably the reaction temperature is about 120° C.

When starting from cis-(XVII), the preferred hydrogen pressure range is from 1500 kPa to 2200 kPa, preferably between 1800 kPa to 2000 kPa. The reaction temperature is between 100° C. and 200° C. preferably at about 125° C. Apparently an equilibrium is reached, typically with a diastereomeric ratio of about 65:35 (trans:cis) as determined by gas chromatography. However via recrystallization it is possible to purify the desired trans-isomer. A suitable solvent for recrystallization is an ether, e.g. diisopropyl ether.

The pure intermediate of formula trans-(XI-1-b) having the trans configuration can also be obtained by chromatographic techniques, such as, for example gravitation chromatography or (H)PLC, starting from the cis/trans mixture of the intermediate (XI-1-b).

Intermediates of formula (XXXV), wherein $PG^2$ is as defined above and X represents OH, NH—PG, $NH_2$, can be prepared by reacting an intermediate of formula (XVIII) with borane or a borane derivative. Borane itself is commercially available e.g. as a borane-tetrahydrofuran complex. Borane derivatives, especially chiral borane derivatives are also commercially available. The reaction with borane is performed in a reaction inert solvent, preferable an ether, e.g. tetrahydrofuran. While adding the borane or the borane derivative the reaction mixture is kept at temperatures below 0° C., interestingly at a temperature of about −30° C. After adding the borane or the borane derivative to the reaction mixture the mixture is allowed to heat up while stirring is continued. The mixture is stirred for several hours. Subsequently, a hydroxide, e.g. sodium hydroxide is added as well as a peroxide, e.g. hydrogen peroxide and the reaction mixture is stirred at elevated temperatures for several hours. After this treatment the reaction product was isolated in art-known manner.

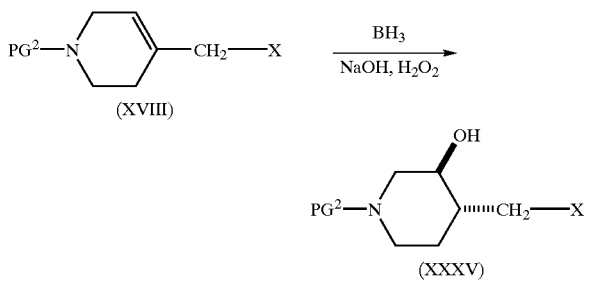

In some cases, it may be appropriate to protect the hydroxy or amine functionality in the intermediates of formula (XVIII) in the above described reaction sequence. Protecting groups for hydroxy or amine functionalities are art-known. These protecting groups may then be removed at the appropriate time during the further synthesis.

Intermediates of formula (XVIII) can be prepared by reacting an intermediate of formula (XXI), wherein $PG^2$ is as defined above and W is a leaving group as defined above, with an intermediate of formula (XXI), wherein X represents OH, $NH_2$, and subsequent reduction of the so-obtained intermediate (XXIII) with sodium borohydride, yielding intermediates of formula (XVIII).

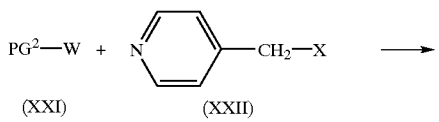

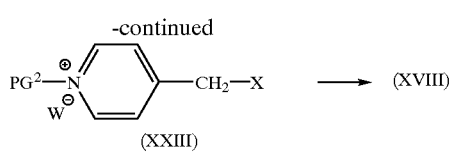

Said reaction procedure can also be used to prepare intermediates of formula (V). Consequently, an intermediate of formula (II) is reacted with an intermediate of formula (XXII) and the so-obtained intermediate of formula (XXIV) is reduced to an intermediate of formula (XXV) using sodium borohydride. Subsequently, the intermediates of formula (XXV) are converted to intermediates of formula (XXVI) using the above-described reaction procedure for the conversion of intermediates (XVIII) to intermediates of formula trans-(XI-b).

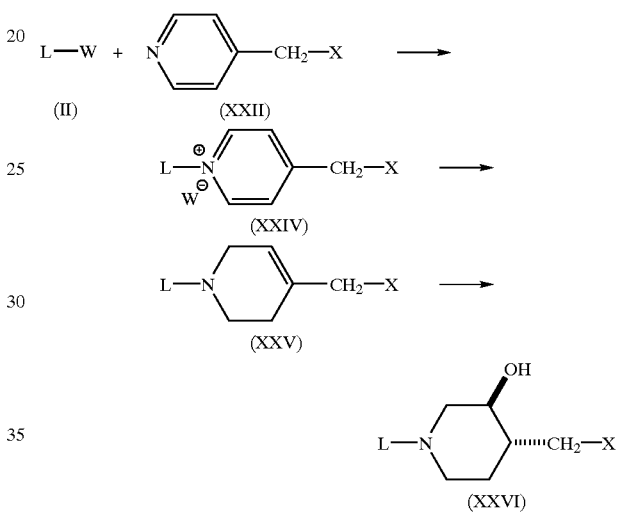

In some cases, it may be appropriate to protect the radial X, i.e. the hydroxy of amine functionality, in the intermediates of formula (XVII), (XXIV), (XXV) or (XXVI) in the above described reaction sequence. Protecting groups for hydroxy or amine functionalities are art-known. These protecting groups may then be removed at the appropriate time during the further synthesis.

Intermediates of formula (XXVI) can be converted to intermediates of formula (V) having the trans configuration, using a reaction procedure as describe above in Scheme 1 or Scheme 2.

Intermediates of formula (VIII-a) are defined as intermediates of formula (VIII) wherein the —$OR^4$ moiety is located on the 4-position of the piperidine moiety and $R^4$ is hydrogen.

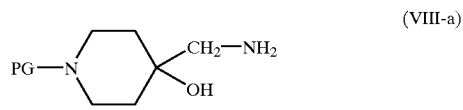

Said intermediates of formula (VIII-a) can be prepared by reacting an intermediate of formula (XXVII) with nitromethane under suitable reaction conditions, such as, e.g. sodium methoxide in methanol, and subsequently converting the nitro group into an amine group, thereby yielding the intermediates of formula (VIII-a).

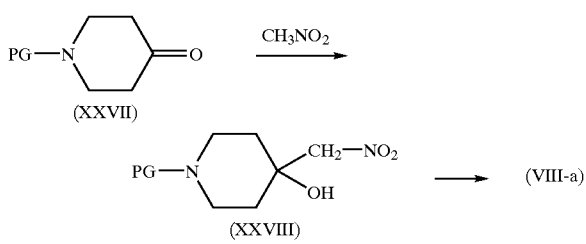

Intermediates of formula (V-a), defined as intermediates of formula (V) wherein $R^5$ is hydrogen and —$OR^4$ is a OH group situated on the 3-position of the piperidine moiety having a trans configuration, can be prepared as following:

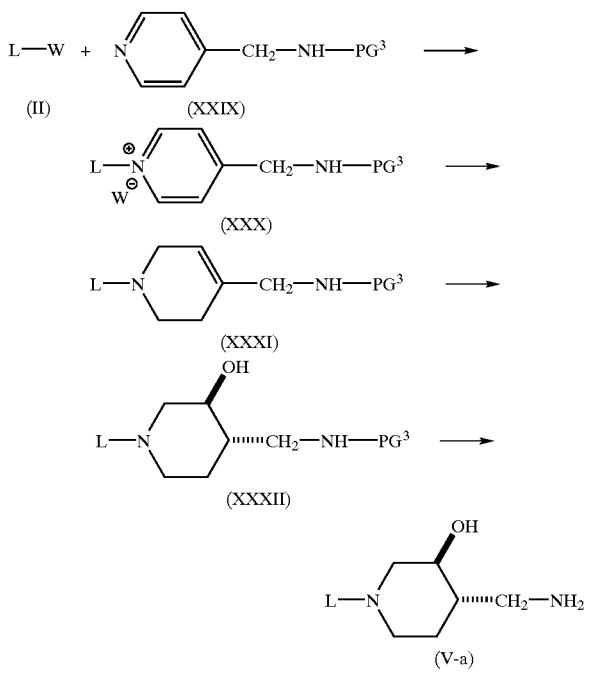

An intermediate of formula (II) is reacted with an intermediate of formula (XXIX), wherein $PG^3$ is a suitable protecting group such as p-toluenesulfonyl, and the so-obtained intermediate of formula (XXX) is reduced to an intermediate of formula (XXXI) using sodium borohydride. Subsequently, the intermediates of formula (XXXI) are converted to intermediates of formula (XXXII) using the above-described reaction procedure for the conversion of intermediates (XVIII) to intermediates of formula trans-(XI-b). Subsequently, removing the protecting group $PG^3$ from intermediates (XXXII) yields the intermediates of formula (V-a).

Intermediates of formula (V-b), defined as intermediates of formula (V) wherein $R^5$ is hydrogen and the —$OR^4$ moiety is situated on the 3-position of the piperidine moiety having a trans configuration, can be prepared by reacting intermediates of formula (XXXIII) with lithium cyanide and subsequent reduction of the intermediates of formula (XXXIV). When the conversion of intermediates (XXXIII) to intermediates (XXIV) is carried out in the presence of a suitable alkylating agent such as, e.g. dimethylsulfate or diethylsulfate, (see for example Example A.10.a) the —$OR^4$ radical is converted from a hydroxy group into an alkyloxy group. In the absence of a suitable alkylating agent, the —$OR^4$ moiety represents a hydroxy group. Conversion from intermediates (XXXIV) to intermediates (V-b) can be done using art-known procedures for converting a cyano group into an amino group (see for example Example A.10.b).

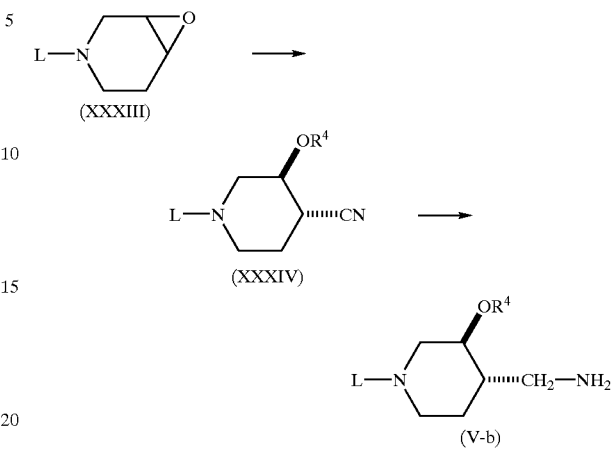

The above described reaction can also be used to make intermediates wherein the radical L is replaced by an appropriate protective group.

The compounds of formula (I), the N-oxide forms, the pro-drugs thereof, the pharmaceutically acceptable salts and stereoisomeric forms thereof possess favourable gastrointestinal properties.

Most of the intermediates of formula (III) have shown to have analogous activity as the final compounds of formula (I).

The favourable gastrointestinal properties of the compounds of the present invention are demonstrated by their $5HT_4$-antagonistic activity as described in Example C.1. The effect on gastric compliance of the present $5HT_4$-antagonistic compounds can be demonstrated in an experiment where gastric compliance is impaired, or decreased, by pre-treatment with a 5-HT transporter inhibitor (e.g. fluvoxamine) and then normalized by administration of a $5HT_4$-antagonistic compound of the present invention. This in vivo experiment is extensively described in WO-97/29739 on pages 8 to 10.

In view of the favourable gastrointestinal properties of the compounds of the present invention, the subject compounds may generally be used in the treatment or prophylaxis of gastrointestinal conditions such as hypermotility, irritable bowel syndrome (EBS), constipation- or diarrhea-predominant IBS, pain- and non-pain- predominant IBS, bowel hypersensitivity, and the reduction of pain associated with gastrointestinal hypersensitivity and/or hyperactivity.

It is also believed that the compounds of formula (I) are useful in the prevention or prophylaxis of dyspepsia. Dyspeptic symptoms are for example epigastric pressure, a lack of appetite, feeling of fullness, early satiety, nausea, vomiting, bloating and gaseous eructation.

In view of the utility of the compounds of formula (I), it follows that the present invention also provides a method of treating warm-blooded animals, including humans, (generally called herein patients) suffering from gastrointestinal conditions such as irritable bowel syndrome (IBS). Consequently a method of treatment is provided for relieving patients suffering from conditions such as hypermotility, irritable bowel syndrome (IBS), constipation- or diarrhea-predominant IBS, pain- and non-pain-predominant IBS, bowel hypersensitivity, and the reduction of pain associated with gastrointestinal hypersensitivity and/or hyperactivity.

The compounds of formula (I) may also be of potential use in other gastrointestinal disorders, such as those associated with upper gut motility. In particular, they are of potential use in the treatment of gastric symptoms of gastro-oesophageal reflux disease, such as heartburn (including episodic heartburn, nocturnal heartburn, and meal-induced heartburn).

Hence, the present invention provides compounds of formula (I) for use as a medicine, and in particular the use of compounds of formula (I) for the manufacture of a medicine for treating gastrointestinal conditions such as hypermotility, IBS, constipation- or diarrhea-predominant EBS, pain- and non-pain predominant IBS, bowel hypersensitivity, and the reduction of pain associated with gastrointestinal hypersensitivity and/or hyperactivity. Both prophylactic and therapeutic treatment are envisaged.

To prepare the pharmaceutical compositions of this invention, an effective amount of the particular compound, in base or acid addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions. These compositions may be administered in various ways, e.g., as a transdermal patch, as a spot-on, as an ointment. Acid addition salts of (I) due to their increased water solubility over the corresponding base form, are obviously more suitable in the preparation of aqueous compositions.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

For oral administration, the pharmaceutical compositions may take the form of solid dose forms, for example, tablets (both swallowable-only and chewable forms), capsules or gelcaps, prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium phosphate); lubricants e.g. magnesium stearate, talc or silica); disintegrants (e.g. potato starch or sodium starch glycollate); or wetting agents (e.g. sodium lauryl sulphate). The tablets may be coated by methods well known in the art.

Liquid preparations for oral administration may take the form of, for example, solutions, syrups or suspensions, or they may be presented as a dry product for constitution with water or other suitable vehicle before use. Such liquid preparations may be prepared by conventional means, optionally with pharmaceutically acceptable additives such as suspending agents (e.g. sorbitol syrup, methylcellulose, hydroxypropyl methylcellulose or hydrogenated edible fats); emulsifying agents (e.g. lecithin or acacia); non-aqueous vehicles (e.g. almond oil, oily esters or ethyl alcohol); and preservatives (e.g. methyl or propyl p-hydroxybenzoates or sorbic acid).

Pharmaceutically acceptable sweeteners comprise preferably at least one intense sweetener such as saccharin, sodium or calcium saccharin, aspartame, acesulfame potassium, sodium cyclamate, alitame, a dihydrochalcone sweetener, monellin, stevioside or sucralose (4,1',6'-trichloro4,1',6'-trideoxygalactosucrose), preferably saccharin, sodium or calcium saccharin, and optionally a bulk sweetener such as sorbitol, mannitol, fructose, sucrose, maltose, isomalt, glucose, hydrogenated glucose syrup, xylitol, caramel or honey.

Intense sweeteners are conveniently employed in low concentrations. For example, in the case of sodium saccharin, the concentration may range from 0.04% to 0.1% (w/v) based on the total volume of the final formulation, and preferably is about 0.06% in the low-dosage formulations and about 0.08% in the high-dosage ones. The bulk sweetener can effectively be used in larger quantities ranging from about 10% to about 35%, preferably from about 10% to 15% (w/v).

The pharmaceutically acceptable flavours which can mask the bitter tasting ingredients in the low-dosage formulations are preferably fruit flavours such as cherry, raspberry, black currant or strawberry flavour. A combination of two flavours may yield very good results. In the high-dosage formulations stronger flavours may be required such as Caramel Chocolate flavour, Mint Cool flavour, Fantasy flavour and the like pharmaceutically acceptable strong flavours. Each flavour may be present in the final composition in a concentration ranging from 0.05% to 1% (w/v). Combinations of said strong flavours are advantageously used. Preferably a flavour is used that does not undergo any change or loss of taste and color under the acidic conditions of the formulation.

The formulations of the present invention may optionally include an anti-flatulent, such as simethicone, alpha-D-galactosidase and the like.

The compounds of the invention may also be formulated as depot preparations. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example as a sparingly soluble salt.

The compounds of the invention may be formulated for parenteral administration by injection, conveniently intravenous, intramuscular or subcutaneous injection, for example by bolus injection or continuous intravenous infusion. Formulations for injection may be presented in unit dosage form e.g. in ampoules or in multidose containers, with an added preservative. The compositions may take such forms as suspensions, solutions or emulsions in oily or aqueous vehicles, and may contain formulatory agents such as isotonizing, suspending, stabilising and/or dispersing agents. Alternatively, the active ingredient may be in powder form for constitution with a suitable vehicle, e.g. sterile pyrogen-free water before use.

The compounds of the invention may also be formulated in rectal compositions such as suppositories or retention enemas, e.g. containing conventional suppository bases such as cocoa butter or other glycerides.

For intranasal administration the compounds of the invention may be used, for example, as a liquid spray, as a powder or in the form of drops.

In general it is contemplated that a therapeutically effective amount would be from about 0.001 mg/kg to about 2 mg/kg body weight, preferably from about 0.02 mg/kg to about 0.5 mg/kg body weight. A method of treatment may also include administering the active ingredient on a regimen of between two or four intakes per day.

Experimental Part

In the procedures described hereinafter the following abbreviations were used: "ACN" stands for acetonitrile; "THF", which stands for tetrahydrofuran; "DCM" stands for dichloromethane; "DIPE" stands for diisopropylether; "EtOAc" stands for ethyl acetate; "$NH_4OAc$" stands for ammonium acetate; "HOAc" stands for acetic acid; "MIK" stands for methyl isobutyl ketone.

For some chemicals the chemical formula was used, e.g. NaOH for sodium hydroxide, $Na_2CO_3$ for sodium carbonate, $K_2CO_3$ for potassium carbonate, $H_2$ for hydrogen gas, MgSO4 for magnesium sulfate, $CuO.Cr_2O_3$ for copper chromite, $N_2$ for nitrogen gas, $CH_2Cl_2$ for dichloromethane, $CH_3OH$ for methanol, $NH_3$ for ammonia, HCl for hydrochloric acid, NaH for sodium hydride, $CaCO_3$ for calcium carbonate, CO for carbon monoxide, and KOH for potassium hydroxide.

A. Preparation of the intermediates

EXAMPLE A.1 a) A solution of 4-pyridinemethanol (1.84 mol) in ACN (1000 ml) was added to a solution of benzylchloride (2.2 mol) in ACN (1000 ml) and the reaction mixture was refluxed for 3 hours, cooled to room temperature and evaporated. The residue was suspended in diethylether, filtered and dried, yielding 1-(phenylmethyl)4-(hydroxy-methyl)-pyridinyl chloride (411 g, 97%).

b) 1-(Phenylmethyl)4-(hydroxymethyl)-pyridinyl chloride(0.87 mol) was dissolved in methanol (2200 ml) and cooled to –20° C. Sodium borohydride (1.75 mol) was added portionwise under a nitrogen atmosphere. The reaction mixture was stirred for 30 minutes and water (200 ml) was added dropwise. The reaction mixture was partially evaporated, water was added and the reaction mixture was extracted with DCM. The organic layer was separated, dried, filtered and evaporated. The residue was purified over silica gel (eluent: DCM), yielding 155 g of 1,2,3,6-tetrahydro-1-(phenylmethyl)4-pyridinemethanol.

EXAMPLE A.2 a) A solution of 1,2,3,6-tetrahydro-1-(phenylmethyl)4-pyridinemethanol (0.5 mol) in THF (1000 ml) was cooled to –30° C. and was added dropwise under a nitrogen atmosphere to a solution of borane in TBF (1 M, 1000 ml) while the reaction mixture was kept at a temperature between –20° C. and –30° C. After the addition, the reaction mixture was stirred for 4 hours, allowed to warm up to room temperature and stirred at room temperature for 18 hours. The reaction mixture was cooled to –10° C. and water (25 ml) was added dropwise. Then, simultaneously, NaOH (3M in water, 70 ml) and the hydrogen peroxide (30 % solution in water, 63.3 ml) was added dropwise while the reaction mixture was kept at a temperature of –10° C. Again NaOH (50 % in water, 140 ml) was added. The reaction mixture was stirred at reflux for 4 hours. The reaction mixture was cooled and filtered. The filtrate was evaporated. The resulting precipitate was dissolved in water (500 ml) and saturated with $K_2CO_3$. The product was extracted with DCM. The resulting solution was dried over $MgSO_4$ and evaporated. The residue was crystallized from DIPE/$CH_3CN$. After several crystallizations (±)-trans-1-(phenyl-methyl)-3-hydroxy4-piperidinemethanol was obtained (Yield: 50.1%)

b) A mixture of (±)-trans-1-(phenylmethyl)-3-hydroxy4-piperidinemethanol (17.8 g, 0.085 mol) (already described in J. Med. Chem., 16, pp. 156–159 (1973)) in methanol (250 ml) was hydrogenated, at 50° C., with palladium on activated carbon (10%, 2 g) as catalyst. After uptake of $H_2$ (1 equivalent), the catalyst was filtered off and the filtrate was evaporated, yielding 12 g of (±)-trans-3-hydroxy4-piperidinemethanol (interm. 1-a) (used in next reaction step without further purification). The corresponding cis-isomer is known from J. Org. Chem., 34, pp. 3674–3676 (1969).

c) A mixture of intermediate (1-a) (0.086 mol) in DCM (250 ml) was stirred at room temperature. A solution of di-tert-butyl dicarbonate (BOC-anhydride) (0.086 mol) in DCM (50 ml) was added dropwise and the resulting reaction mixture was stirred at room temperature. An oil precipitated. Methanol (60 ml) was added and the resulting reaction solution was stirred for 60 min at room temperature. The solvent was evaporated. The residue was crystallized from DIPE. The precipitate was filtered off and dried, yielding 13.7 g (68.8%) of 1,1-dimethylethyl (trans)-3-hydroxy4-(hydroxymethyl)-1-piperidinecarboxylate (intermediate 1-b).

d) Intermediate (1-b) (0.087 mol) was dissolved in chloroform (400 ml) and pyridine (7.51 ml). The solution was cooled to 0° C. 4-Methyl-benzenesulfonyl chloride (0.091 mol) was added portionwise over 20 minutes. The reaction mixture was stirred and refluxed for 16 hours. More 4-methyl-benzenesulfonyl chloride (1.7 g) and pyridine (1.4 ml) were added and the resulting reaction mixture was stirred and refluxed for 6 hours, then cooled, washed with citric acid (10% w/w in $H_2O$), washed with brine, dried, filtered and the solvent was evaporated. The residue was purified by flash column chromatography over silica gel (eluent:DCM).

The desired fractions were collected and the solvent was evaporated, yielding 9 g of (intermediate 1-c) as a colorless oil. Intermediate (1-c) (0.13 mol) was separated into its enantiomers by chiral column chromatography over a dynamic axial compression column with Chiralcel AD (20 μm, 100 Å, code 061347) (room temperature, column diameter: 11 cm; eluent: hexane/ethanol 80/20; 50 g product in 5 liters of eluent). Two fraction groups were collected and their solvent was evaporated, yielding 26.2 g of a first eluting fraction fraction (I) and 26 g of a second eluting fraction (II). Fraction (II) was crystallized from DIPE, filtered off and dried, yielding 12.5 g of (+)-1,1-dimethylethyl (trans)-3-hydroxy-4-[[(4-methylphenyl)sulfonyl] oxymethyl]-1-piperidinecarboxylate [intermediate (1-c-I); $[\alpha]_D^{20}=+13.99°$ (c=27.87 mg/5 ml in $CH_3OH$)].

Fraction (II) was crystallized from DIPE, filtered off and dried, yielding 15 g of (−)-1,1-dimethylethyl (trans)-3-hydroxy4-[[(4-methylphenyl)sulfonyl]oxymethyl]-1-piperidinecarboxylate [intermediate (1-c-II); $[\alpha]_D^{20}=-38.46°$ (c=25.35 mg/5 ml in $CH_3OH$)].

e) A mixture of intermediate (1-c) (0.023 mol) and benzylamine (0.084 mol) in THF (100 ml) was stirred for 16 hours at 125° C. (autoclave). The reaction mixture was cooled. The solvent was evaporated. The residue was partitioned between DCM and an aqueous $K_2CO_3$ solution. The organic layer was separated, dried, filtered and the solvent was evaporated, yielding 15.4 g of 1,1-dimethylethyl (trans)-3-hydroxy4-[[(phenylmethyl)amino]methyl]-1-piperidinecarboxylate (intermediate 1-d).

f) A mixture of intermediate (1-d) (max. 0.023 mol crude residue) in methanol (100 ml) was hydrogenated with palladium-on-carbon (10%, 1 g) as a catalyst. After uptake of $H_2$ (1 equivalent), the catalyst was filtered off and the filtrate was evaporated. The residue was solidified in DIPE+ACN, filtered off and dried (vacuum, 40° C.), yielding 4 g (76%) of 1,1-dimethylethyl (trans)4-(aminomethyl)-3-hydroxy-1-piperidinecarboxylate (intermediate 1-e, mp. 178° C.).

In an analogous way, but starting from cis-3-hydroxy4-piperidinemethanol (described in *J. Org. Chem.*, 34, pp. 3674–3676 (1969)), 1,1-dimethylethyl (cis)4-(aminomethyl)-3-hydroxy-1-piperidinecarboxylate (interm. 1-f) was prepared.

EXAMPLE A.3

A solution of 5-chloro-2,3-dihydro-7-benzofurancarboxylic acid (0.14 mol) in chloroform (500 ml) was cooled to <10 ° C. and triethyl amine (0.14 mol) was added. Then, ethoxycarbonyl chloride (0.14 mol) was added at <10 ° C. The mixture was. stirred for 45 min at <10 ° C., giving mixture (A). Intermediate (1-f) (0.14 mol) was stirred in chloroform (250 ml), giving mixture (B). Mixture (A) was added to mixture (B) at <10° C. The reaction mixture was stirred for 30 minutes, washed with 5% NaOH, with water, then dried, filtered and the solvent was evaporated. The residue was crystallized from ACN, then cooled to 0° C. and the resulting precipitate was filtered off and dried, yielding 26 g of (±)-1,1-dimethylethyl (cis)4-[[[(5-chloro-2,3-dihydro-7-benzofuranyl)carbonyl]amino]methyl]-3-hydroxy-1-piperidinecarboxylate (interm. 2).

EXAMPLE A.4

A mixture of intermediate (2) (0.068 mol) in a mixture of HCl/2-propanol (80 ml) and 2-propanol (800 ml) was stirred and refluxed for 45 minutes, then cooled and the solvent was evaporated. The residue was crystallized from a mixture of 2-propanol and water, then cooled to 0° C. and the precipitate was filtered off and dried, yielding 16 g (76%) of (±)-(cis)-5-chloro-2,3-dihydro-N-[(3-hydroxy4-piperidinyl) methyl]-7-benzofuran-carboxamide monohydrochloride (interm. 3-a, mp. 230° C.).

EXAMPLE A.5

A mixture of ethyl 4-[[[(7-chloro-2,3-dihydro-1,4-benzodioxin-5-yl)carbonyl]-amino]methyl]-3-methoxy-1-piperidinecarboxylate (0.051 mol) and potassium hydroxide (0.5 mol) in ethanol (200 ml) was stirred and refluxed for 30 hours and then cooled. The solvent was evaporated. The residue was dissolved in water and the solvent was evaporated again. The residue was partitioned between DCM and water. The organic layer was separated, dried, filtered, and the solvent was evaporated. The residue was purified by column chromatography over silica gel (eluent : $CH_2Cl_2/(CH_3OH/NH_3)$93/7). The pure fractions were collected and the solvent was evaporated, yielding 9 g of (cis)-7-chloro-2,3-dihydro-N-[(3-methoxy-4-piperidinyl)methyl]-1,4-benzodioxin-5-carboxamide (interm. 3-i). Part of interm. (3-i) was dissolved in 2-propanol and converted into the ethanedioic acid salt (1:1). The precipitate was filtered off and dried, yielding 1.2 g of (cis)-7-chloro-2,3-dihydro-N-[(3-methoxy4-piperidinyl)methyl]-1,4-benzodioxin-5-carboxamide ethanedioate (1:1) (interm. 3-j, mp. 208° C.).

EXAMPLE A.6 a) A mixture of ethyl 4-(aminomethyl)-4-hydroxy-1-piperidinecarboxylate (0.125 mol) and potassium hydroxide (1.25 mol) in 2-propanol (700 ml) was stirred and refluxed for 6 hours. The reaction mixture was cooled and the solvent was evaporated. The residue was taken up into water, then extracted with DCM with a small amount of methanol. The mixture was salted out with NaCl. The separated organic layer was dried, filtered and the solvent evaporated, yielding: 11.2 g of intermediate (4).

b) A mixture of intermediate (4) (0.1 mol), 2-(bromomethyl)-1,3-dioxolane (0.1 mol) and $Na_2CO_3$ (0.2 mol) in ACN (1000 ml) stirred and refluxed for 24 hours. The reaction mixture was cooled. The precipitate was filtered off, washed and the filtrate was evaporated. The residue was purified over silica gel on a glass filter (eluent: $CH_2Cl_2/(CH_3OH/NH_3)$ 90/10). The pure fractions were collected and the solvent was evaporated, yielding 8.2 g of 4-(aminomethyl)-1-(1,3-dioxolan-2-ylmethyl)-4-piperidinol (intermediate 5, mp. 137° C.).

EXAMPLE A.7 a) A mixture of intermediate (1-d) (0.33 mol) in a mixture of HCl in 2-propanol (500 ml) and 2-propanol (2500 ml) was stirred and refluxed for 30 minutes. The reaction mixture was cooled, and the solvent was evaporated. The residue was taken up in $CH_2Cl_2/CH_3OH(H_2O/NH_3)$. The organic layer was separated, dried, filtered and the solvent was evaporated. The residue was purified by column chromatography over silica gel (eluent: $CH_2Cl_2/CH_3OH$ 90/10 and $CH_2Cl_2/(CH_3OH/NH_3)$ 90/10). The pure fractions were collected and the solvent was evaporated, yielding 49 g of intermediate (trans)4-[[(phenylmethyl)amino]methyl]-3-piperidinol (intermediate 6).

b) A mixture of 2-(2-bromoethyl)-1,3-dioxolane (0.04 mol), intermediate (6) (0.04 mol) and $Na_2CO_3$ (10%, 0.08 mol) in MIK (400 ml) was stirred and refluxed for 20 hours and then cooled. The solvent was evaporated. The residue was taken up in DCM and water. The organic layer was separated, dried, filtered and the solvent was evaporated. The residue was purified by column chromatography over silica gel (eluent: $CH_2C_2/(CH_3OH/NH_3)$ 96/4). The pure fractions were collected and the solvent was evaporated. Toluene was added and evaporated again, yielding 6 g of (trans)-1-[2-(1,3-dioxolan-2-yl)ethyl]-4-[[(phenylmethyl)amino]methyl]-3-piperidinol (intermediate 7).

c) A mixture of intermediate (7) (0.019 mol) in methanol (150 ml) was hydrogenated with palladium-on-carbon (10%, 2 g) as a catalyst. After uptake of hydrogen (1 equivalent), the catalyst was filtered off and the filtrate was evaporated, yielding 4 g of (trans)4-(aminomethyl)-1-[2-(1,3-dioxolan-2-yl)ethyl]-3-piperidinol (intermediate 8).

EXAMPLE A.8 a) A mixture of methanol (60 ml) and sulfuric acid (5.2 ml) was stirred at room temperature. 5-Chloro-2,3-dihydroxybenzoic acid (0.11 mol) was added. The reaction mixture was stirred and refluxed for 20 hours, and then poured out onto ice. The precipitate was filtered off, washed with water, and dried, yielding 18.48 g of methyl 5-chloro-2,3-dihydroxybenzoate (intermediate 9; mp: 102° C.).

b) A mixture of intermediate (9) (0.3 mol), 1,3-dibromopropane (0.42 mol) and $K_2CO_3$ (0.66 mol) in 2-propanone (500 ml) was stirred and refluxed for 20 hours, then filtered hot and the filtrate was evaporated. The residue was purified by column chromatography over silica gel (eluent : DCM). The desired fractions were collected and the solvent was evaporated. Toluene was added and azeotroped on the rotary evaporator, yielding 69 g of methyl 8-chloro-3,4-dihydro-2H-1,5-benzodioxepin-6- carboxylate (intermediate 10).

c) A mixture of intermediate (10) (0.25 mol) and potassium hydroxide (1 mol) in water (650 ml) was stirred and refluxed for 2 hours. The reaction mixture was cooled, acidified with HCl and the resulting precipitate was filtered off, washed with water, and dried, yielding 48 g of 8-chloro-3,4-dihydro-2H-1,5-benzodioxepin-6-carboxylic acid (intermediate 11).

EXAMPLE A.9 a) Intermediate (11) (0.1 mol), triethylamine (0.1 mol) and DCM (500 ml) were stirred at a temperature below 10° C. Ethyl chloroformate (0.1 mol) was added dropwise at temperature below 10° C. The mixture was stirred for 30 minutes at a temperature below 10° C. A solution of 1,1-dimethylethyl (3S-trans)-4-(aminomethyl)-3-hydroxy-1-piperidinecarboxylate (0.1 mol) in triethylamine (250 ml) was added at a temperature below 10° C. The reaction mixture was stirred for one hour at room temperature. The mixture was concentrated to half the initial volume. The concentrate was washed with water, with $H_2O/50\%$ NaOH, and again with water. The organic layer was separated, dried, filtered and the solvent was evaporated, yielding 44 g of 1,1-dimethylethyl(3S-trans)-4-[[[(8-chloro-3,4-dihydro-2H-1,5-benzodioxepin6-yl)carbonyl]amino]methyl]-3-hydroxy-1-piperidinecarboxylate monohydrate (intermediate 12) (mp: 88° C.; sticky) $[\alpha]_D^{20}=-0.97°$ (c=25.71 mg/5 ml in $CH_3OH$).

b) A mixture of intermediate (12) (0.095 mol) in a mixture of HCl in 2-propanol (100 ml) and HCl (500 ml) was stirred and refluxed for one hour. The reaction mixture was cooled. The solvent was evaporated. The residue was taken up into DCM and washed with $NH_3/H_2O$. The organic layer was separated, dried, filtered and the solvent was evaporated. The residue was purified over silica gel on a glass filter (eluent $CH_2Cl_2/(CH_3OH/NH_3)$ 90/10). The product fractions were collected and the solvent was evaporated. A sample (2 g) of this fraction was crystallized from DIPE with a small amount of ACN, filtered off, washed and dried, yielding 1.8 g of (3S-trans)-8-chloro-3,4-dihydro-N-[(3-hydroxy4-piperidinyl)methyl]-2H-1,5-benzodioxepin-6-carboxamide (intermediate 3-t) (mp: 114 ° C.) $[\alpha]_D^{20}=-14.34°$ (c=24.41 mg/5 ml in $CH_3OH$).

EXAMPLE A.10 a) Reaction was carried out under a nitrogen atmosphere. Lithium hydride (95%) (0.036 mol) was suspended in THF (30 ml). A solution of 2-hydroxy-2-methyl-propanenitrile (0.036 mol) in TEF (10 ml) was added dropwise (evolution of hydrogen gas). The mixture was stirred for 90 minutes at room temperature. A solution of 7-oxa-3-azabicyclo[4.1.0]heptane-3-carboxylic acid, ethyl ester (0.03 mol) in THF (15 ml) for 90 minutes. The reaction mixture was cooled to 15 ° C. Diethyl sulfate (0.039 mol) was added (exothermic temperature rise to 25 ° C.). The reaction mixture was stirred for one hour at room temperature, then stirred and refluxed for 6 hours, cooled and a drop of water was added. The solvent was evaporated. The residue was partitioned between water and DCM. The organic layer was separated, dried, filtered and the solvent was evaporated. The residue was purified by column chromatography over silica gel (eluent: $CH_2C]_2/CH_3OH$ from 100/0 to 99/1). The pure fractions were collected and the solvent was evaporated, yielding 4.3 g of ethyl (trans)-4-cyano-3-ethoxy-1-piperidine-carboxylate (intermediate 13).

b) A mixture of intermediate (13) (0.19 mol) in methanol saturated with $NH_3$ (500 ml) was hydrogenated at 14° C. with Raney nickel as a catalyst. After uptake of hydrogen (2 equivalents), the catalyst was filtered off and the filtrate was evaporated. The residue was purified by column chromatography over silica gel (eluent: $CH_2Cl_2/(CH_3OH/NH_3)$ 95/5). The desired fractions were collected and the solvent was evaporated, yielding 12 g of ethyl (trans)-4-(aminomethyl)-3-ethoxy-1-piperidinecarboxylate (intermediate 14).

c) At a temperature below 10° C., triethylamine (0.01 mol) was added to 7-chloro-2,3-dihydro-1,4-benzodioxin-5-carboxylic acid (0.01 mol) in chloroform (40 ml). Ethyl chloroformate 01 ml) was added at a temperature below 10IC and the mixture was stirred for 30 minutes at a temperature below 10° C. This mixture was added to a solution of intermediate (14) (0.01 mol) in chloroform (20 ml), at a temperature below 10° C. The reaction mixture was stirred for 30 minutes then washed with a 5% HCl solution, with water, dried, filtered and the solvent was evaporated, yielding 4 g of (trans)-ethyl 4-[[[(7-chloro-2,3-dihydro-1,4-benzodioxin-5-yl)carbonyl]-amino]methyl]-3-ethoxy-1-piperidinecarboxylate (intermediate 15).

d) Intermediate (15) was converted into intermediate (3-p) using the procedure as described in Example A.5.

In this manner and in a similar manner were prepared:

TABLE I-1

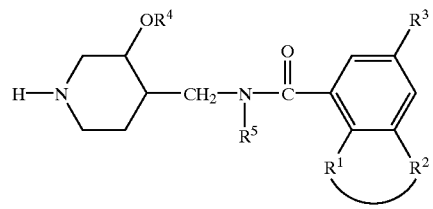

| Int. No. | Ex. No. | -R¹-R²- | R³ | —OR⁴ | Physical data |
|---|---|---|---|---|---|
| 3-a | A.4 | —O—(CH$_2$)$_2$— | Cl | —OH | cis; .HCl, mp. 230° C. |
| 3-b | A.4 | —O—(CH$_2$)$_2$— | Cl | —OH | trans; .C$_2$H$_2$O$_4$, mp. 230° C. |
| 3-c | A.4 | —O—(CH$_2$)$_2$—O— | Cl | —OH | trans; |
| 3-d | A.4 | —O—(CH$_2$)$_2$—O— | Cl | —OH | cis |
| 3-e | A.4 | —O—(CH$_2$)$_2$—O— | Cl | —OH | cis; .C$_2$H$_2$O$_4$ |
| 3-f | A.4 | —O—(CH$_2$)$_3$—O— | Cl | —OH | trans |
| 3-g | A.4 | —O—(CH$_2$)$_3$—O— | Cl | —OH | trans, .C$_2$H$_2$O$_4$, mp. 196° C. |
| 3-h | A.4 | —O—(CH$_2$)$_4$—O— | Cl | —OH | trans, .H$_2$O |
| 3-i | A.5 | —O—(CH$_2$)$_2$—O— | Cl | —OCH$_3$ | cis |
| 3-j | A.5 | —O—(CH$_2$)$_2$—O— | Cl | —OCH$_3$ | cis; .C$_2$H$_2$O$_4$, mp. 208° C. |
| 3-k | A.5 | —O—(CH$_2$)$_3$—O— | Cl | —OCH$_3$ | cis |
| 3-l | A.5 | —O—(CH$_2$)$_3$—O— | Cl | —OCH$_3$ | cis; .C$_2$H$_2$O$_4$, mp. 201° C. |
| 3-m | A.4 | —O—(CH$_2$)$_3$—O— | Cl | —OCH$_3$ | trans |
| 3-n | A.4 | —O—(CH$_2$)$_3$—O— | Cl | —OCH$_3$ | trans; .C$_2$H$_2$O$_4$ (2:1), mp. 252° C. |
| 3-o | A.4 | —O—(CH$_2$)$_3$—O— | Cl | —OC$_2$H$_5$ | trans; mp. 86° C. |
| 3-p | A.10 | —O—(CH$_2$)$_2$—O— | Cl | —OC$_2$H$_5$ | trans; mp. 122° C. |
| 3-q | A.10 | —O—CH$_2$—O— | Cl | —OC$_2$H$_5$ | trans; mp. 106° C. |
| 3-r | A.5 | —O—CH$_2$—O— | Cl | —OCH$_3$ | trans; .C$_2$H$_2$O$_4$; mp. 172° C. |
| 3-s | A.4 | —O—(CH$_2$)$_2$— | Cl | —OH | trans; .HCl |
| 3-t | A.9 | —O—(CH$_2$)$_3$—O— | Cl | —OH | (3S-trans); mp. 114° C.; $[\alpha]^{20}_D = -14.34°$ (c = 24.41 mg/5 ml in CH$_3$OH) |
| 3-w | A.9 | —O—(CH$_2$)$_3$—O— | Cl | —OH | (3R-trans); $[\alpha]^{20}_D = +11.50°$ (c = 24.78 mg/5 ml in CH$_3$OH) |

.C$_2$H$_2$O$_4$ stands for the ethanedioate salt

TABLE I-1a

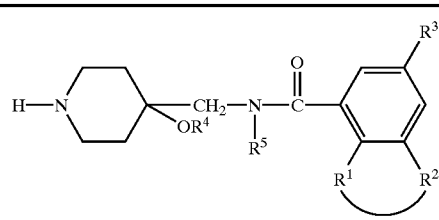

| Int. No. | Ex. No. | -R¹-R²- | R³ | —OR⁴ | Physical data |
|---|---|---|---|---|---|
| 3-u | A.4 | —O—(CH$_2$)$_3$—O— | Cl | —OH | .HCl, mp. 210° C. |
| 3-v | A.5 | —O—(CH$_2$)$_2$—O— | Cl | —OH | .HCl.H$_2$O, mp. 150° C. |

B. Preparation of the final compounds

EXAMPLE B.1

A mixture of 3-chloropropyl methyl ether (0.014 mol), intermediate (3c) (0.01 mol) and Na$_2$CO$_3$ (0.02 mol) in methyl isobutylketone (100 ml) was stirred and refluxed for 20 hours and then cooled. The solvent was evaporated. The residue was partitioned between DCM and H$_2$O. The organic layer was separated, dried, filtered, and the solvent was evaporated. The residue was purified by column chromatography over silica gel (eluent: CH$_2$Cl$_2$/(CH$_3$OH/NH$_3$) 95/5). The pure fractions were collected and the solvent was evaporated. The residue was suspended in DIPE, filtered off and dried, yielding 0.8 g (21 %) of (+)-(trans)-7-chloro-2,3-dihydro-N-[[3-hydroxy-1-(3-methoxy-propyl)4-piperidinyl]methyl]-1,4-benzodioxin-5-carboxamide (comp. 67, mp.+110° C.).

EXAMPLE B.2

A mixture of intermediate (3-c) (0.01 mol) and butyraldehyde (0.014 mol) in methanol (150 ml) was hydrogenated with platinum on carbon (5%, 1 g) as a catalyst in the presence of thiophene (4%, 2 ml). After uptake of hydrogen gas (1 equivalent), the catalyst was filtered off and the filtrate was evaporated. The residue was partitioned between DCM and H$_2$O. The organic layer was separated, dried, filtered, and the solvent was evaporated. The residue was purified by column chromatography over silica gel (eluent: CH$_2$C$_2$/(CH$_3$OH/NH$_3$) 95/5). The pure fractions were collected and the solvent was evaporated. The residue was suspended in DIPE, filtered off and dried, yielding 1.4 g (37%) of (±)-(trans)-N-[(1-butyl-3-hydroxy4-piperidinyl)methyl]-7-chloro-2,3-dihydro-1,4-benzodioxin-5-carboxamide (comp. 64, mp. 112° C.).

EXAMPLE B.3

A mixture of intermediate (3-c) (0.04 mol) and acrylonitrile (0.05 mol) in 2-propanol (80 ml) was stirred and refluxed for 2 hours. The reaction mixture was cooled and the solvent was evaporated. The residue was purified by column chromatography over silica gel (eluent: $CH_2Cl_2$/($CH_3OH/NH_3$) 95/5). The residue was suspended in DIPE, filtered off and dried, yielding 7.1 g of (±)-(trans)-7-chloro-N-[[1-(2-cyanoethyl)-3-hydroxy-4-piperidinyl]methyl]-2,3-dihydro-1,4-benzodioxin-5-carboxamide (comp. 73).

EXAMPLE B.4

A mixture of compound (73) (0.019 mol) in a mixture of $NH_3$/$CH_3OH$ (300 ml) was hydrogenated with Raney nickel (3 g) as a catalyst. After uptake of hydrogen gas (2 equivalents), the catalyst was filtered off and the filtrate was evaporated, yielding 6 g of (±)-trans-N-[[1-(3-aminopropyl)-3-hydroxy-4-piperidinyl]methyl-7-chloro-2,3-dihydro-1,4-benzodioxin-5-carboxamide (compound 76).

EXAMPLE B.5

A mixture of 2-chloro-3-methyl-pyrazine (0.011 mol), compound (76) and calciumoxide (0.011 mol) was stirred for 6 hours at 120° C., then cooled. The residue was dissolved in a small amount of DCM. The resulting precipitate was filtered off and the filtrate was purified by column chromatography over silica gel (eluent: $CH_2Cl_2$/($CH_3OH$/$NH_3$) 95/5). The pure fractions were collected and the solvent was evaporated. The residue was crystallized from ACN, filtered off and dried, yielding 0.6 g (16%) of (±)-(trans)-7-chloro-2,3-dihydro-N-[[3-hydroxy-1-[3-[(3-methyl-2-pyrazinyl)amino]propyl]-4-piperidinyl]methyl]-1,4-benzodioxin-5-carboxamide (comp. 84, mp.±185° C.).

EXAMPLE B.6

A mixture of compound (70) (0.007 mol) and HCl (8 ml) in THF (80 ml) was stirred and refluxed for one hour, cooled, poured out into $NH_3$/$H_2O$ and this mixture was extracted with DCM. The organic layer was removed, dried, and the solvent was evaporated. The residue was purified by column chromatography over silica gel (eluent: $CH_2Cl_2$/($CH_3OH$/$NH_3$) 95/5). The desired fractions were collected and the solvent was evaporated. The residue was solidified in DIPE with a drop of ACN, cooled to 0° C., filtered off and dried, yielding 1.7 g (60%) of (+)-(trans)-7-chloro-2,3-dihydro-N-[[3-hydroxy-1-(4-oxopentyl)4-piperidinyl]methyl]-1,4-benzodioxin-5-carboxamide (comp. 65).

EXAMPLE B.7

A mixture of compound (75) (0.012 mol) and 4-hydroxy-2-methylthiopyrinidine (0.017 mol) in dimethylacetamide (DMA) (6 ml) was stirred for 3 hours at 130° C., then cooled and partitioned between $CH_2Cl_2$/$H_2O$. The organic layer was separated, dried, filtered and the solvent was evaporated. The residue was purified by column chromatography over silica gel (eluent: $CH_2Cl_2$/$CH_3OH$ 90/10). The pure fractions were collected and the solvent was evaporated. The residue was suspended in DIPE, filtered off and dried. This fraction was stirred in boiling DIPE, filtered off and dried, yielding 0.58 g (10%) of (trans)-7-chloro-2,3-dihydro-N-[[3-hydroxy-1-[2-[(4-hydroxy-2-pyrimidinyl)amino]ethyl] 4-piperidinyl]methyl]-1,4-benzodioxin-5-carboxamide monohydrate (comp. 85).

EXAMPLE B.8

A mixture of compound (23) (0.0084 mol), 2-chloro4-methoxypyrimidine (0.0106 mol) and $K_2CO_3$ (0.017 mol) in 1-butanol (25 ml) was stirred and refluxed for 14 hours. The reaction mixture was cooled. Water (100 ml) was added. This mixture was extracted with DCM (3×80 ml). The separated organic layer was dried, filtered and the solvent evaporated. The residue was purified by short column chromatography over silica gel (eluent: $CH_2Cl_2$/($CH_3OH/NH_3$) from 97/3 to 95/5). The pure fractions were collected and the solvent was evaporated, yielding 3.60 g (90%) of compound (25).

EXAMPLE B.9

A mixture of compound (25) (0.0075 mol) and HCl (36%) 0.075 mol) in water (35 ml) was stirred and refluxed for 4 hours. The reaction mixture was cooled. DCM (35 ml) was added. An aqueous $NH_3$ solution was added dropwise until pH>9. Precipitation resulted. The solvents were decanted. The precipitate was dissolved in methanol, filtered over a glass filter and concentrated. The residue was crystallized from $CH_3OH/CH_3CN$, filtered off, dried, recrystallized from $CH_3CN/CH_3OH$, filtered off and dried, yielding 1.63 g of compound (26) (mp:>160 ° C.).

EXAMPLE B.10

A mixture of 7-chloro-2,3-dihydro-1,4-benzodioxin-5-carboxylic acid (0.009 mol) and triethylamine (0.009 mol) in DCM (50 ml) was stirred at 5° C. Ethyl chloroformate (0.009 mol) was added dropwise at 5° C. The mixture was stirred for 30 min at 5° C. A solution of intermediate (5) (0.009 mol) in DCM (20 ml) was added at 5° C. The reaction mixture was stirred for 1 hour at room temperature. The reaction mixture was washed with water, with a 5% aqueous NaOH solution and again with water. The separated organic layer was dried, filtered and the solvent evaporated. The residue was purified by column chromatography over silica gel (eluent: $CH_2Cl_2$/($CH_3OH/NH_3$) 96/4). The desired fractions were collected and the solvent was evaporated. The residue was crystallized from DIPE+ACN, filtered off, washed and dried, yielding 1.84 g of compound (102) (mp: 137° C.).

EXAMPLE B.11

Ethylene oxide (gas) was bubbled through a mixture of intermediate (3-f) (0.01 mol) in methanol (100 ml) for 1 hour. The solvent was evaporated. The residue was purified by column chromatography over silica gel (eluent: $CH_2Cl_2$/$CH_3OH$ 92/8). The pure fractions were collected and the solvent was evaporated. The residue was solidified in DIPE, a drop of ACN and a drop of water. The precipitate was filtered off and dried at 40° C., yielding 1.3 g of compound (147) (mp.108° C.).

EXAMPLE B.12

A mixture of compound (155) (0.03 mol), THF (150 ml), water (150 ml) and Amberlite IRA400 (OH⁻) (60 g) was stirred for 22 hours at room temperature. The solvent was removed by filtration. The residue was washed with water, THF, again with water, then stirred for 30 minutes in HCl (1 N, 75 ml) (3×; the Amberlite was filtered off each time). The solvent was decanted. The residue was crystallized from ACN, filtered off, washed and dried, yielding 3.25 g of compound (156) (mp. 142 ° C.).

EXAMPLE B.13

Compound (158) (0.0088 mol), triethylamine (0.01 mol) and chloroform (100 ml) were stirred at a temperature below 10° C. A solution of ethoxycarbonyl chloride (0.009 mol) in chloroform (10 ml) was added dropwise at a temperature below 10° C. The reaction mixture was stirred for one hour at room temperature. The mixture was washed with water. The organic layer was separated, dried, filtered and the solvent was evaporated. The residue was purified over silica gel on a glass filter (eluent: $CH_2Cl_2/(CH_3OH/NH_3)$ 95/5). The product fractions were collected and the solvent was evaporated. The residue was crystallized from DIPE+ACN and a small amount of water, filtered off, washed and dried, yielding 2.73 g of compound (159) (mp: sticky at 70° C.).

Table F-1 to F-5a list the compounds that were prepared according to one of the above Examples. The following abbreviations were used in the tables: $.C_2H_2O_4$ stands for the ethanedioate salt, $.(E)-C_4H_4O_4$ stands for the (E)-2-butenedioate salt, and $.(Z)-C_4H_4O_4$ stands for the .(Z)-2-butenedioate salt.

TABLE F-1

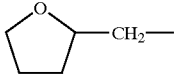

| Co. No. | Ex. No. | —L | OR⁴ | Physical data |
|---|---|---|---|---|
| 1 | B.2 | $CH_3(CH_2)_3—$ | OH | cis; mp. 100° C. |
| 2 | B.2 | $CH_3(CH_2)_3—$ | OH | trans, mp. 101–103° C. |
| 3 | B.1 | $CH_3O(CH_2)_3—$ | OH | cis; mp. 94° C. |
| 4 | B.1 | $CH_3O(CH_2)_3—$ | OH | trans, mp. 117° C. |
| 5 | B.6 | $CH_3—CO—(CH_2)_3—$ | OH | trans; mp. 104–106° C. |
| 6 | B.1 | $HO—(CH_2)_3—$ | OH | trans |
| 7 | B.1 | 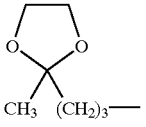 | OH | trans |
| 8 | B.1 | 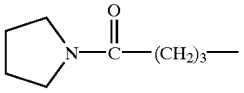 | OH | trans; $.H_2O$ (1:1); mp. 88–92° C. |
| 9 | B.1 | 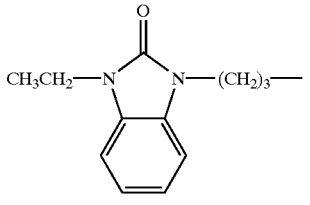 | OH | trans; mp. >70° C.; $.H_2O$ (1:1) |
| 10 | B.1 | $NC—(CH_2)_3—$ | OH | trans; mp. 172° C. |
| 11 | B.2 | $C_6H_5—CH_2—$ | OH | cis; mp. 110° C. |
| 12 | B.2 | $C_6H_5—CH_2—$ | OH | trans; mp. 149° C. |
| 13 | B.1 | $4\text{-F}—C_6H_5—O—(CH_2)_3—$ | OH | cis |
| 14 | B.1 | $4\text{-F}—C_6H_5—O—(CH_2)_3—$ | OH | trans; mp. 137° C. |
| 15 | B.1 | $C_6H_5—CO—CH_2—$ | OH | trans |
| 16 | B.1 | 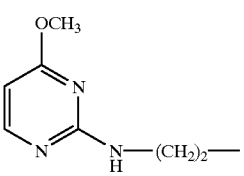 | OH | trans; mp. 168–170° C. |
| 17 | B.1 | $CH_3—SO_2—NH—(CH_2)_2—$ | OH | trans; mp. 147° C. |
| 18 | B.1 | $NC—CH_2—$ | OH | trans |
| 19 | B.4 | $NH_2—(CH_2)_2—$ | OH | trans |
| 20 | B.8 |  | OH | trans |

TABLE F-1-continued

[Structure: L—N(piperidine with OR⁴)—CH₂—NH—C(=O)—(5-chloro-2,3-dihydrobenzofuran-7-yl)]

| Co. No. | Ex. No. | —L | OR⁴ | Physical data |
|---|---|---|---|---|
| 21 | B.9 | 2-(pyrimidin-4(3H)-on-2-ylamino)ethyl: [pyrimidinone]-NH-(CH₂)₂— | OH | trans; .H₂O (1:1) |
| 22 | B.3 | NC—(CH₂)₂— | OH | trans; mp. 158° C. |
| 23 | B.4 | NH₂—(CH₂)₃— | OH | trans |
| 24 | B.8 | (3-methylpyrazin-2-yl)-NH—(CH₂)₃— | OH | trans |
| 25 | B.8 | (4-methoxypyrimidin-2-yl)-NH—(CH₂)₃— | OH | trans |
| 26 | B.9 | [pyrimidin-4(3H)-on-2-yl]-NH—(CH₂)₃— | OH | trans; .HCl (1:1); .H₂O (1:1); mp. >160° C. |
| 27 | B.5 | (3-methylpyrazin-2-yl)-NH—(CH₂)₂— | OH | trans; .C₂H₂O₄ (1:1) .2-propanolate (1:1) |
| 28 | B.1 | (1,3-dioxolan-2-yl)-CH₂— | OH | trans; .H₂O (1:2); mp. 75° C. |
| 29 | B.1 | HO—(CH₂)₂—O—(CH₂)₂— | OH | trans; mp. 122° C. |
| 30 | B.10 | (1,3-dioxolan-2-yl)-(CH₂)₂— | OH | trans; mp. 126° C. |
| 31 | B.1 | CH₃O—CO—(CH₂)₃— | OH | trans; mp. 98° C. |
| 32 | B.6 | HO—CO—(CH₂)₃— | OH | trans; .HCl (1:1); mp. 228° C. |
| 33 | B.1 | CH3—O—CO—(CH₂)₂— | OH | trans; .H₂O (1:1) |
| 34 | B.1 | CH3—O—CO—(CH₂)₄— | OH | trans; .HBr (1:1); mp. 211° C. |

TABLE F-1a

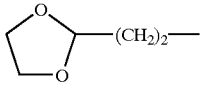

| Co. No. | Ex. No. | —L | OR⁴ | Physical data |
|---|---|---|---|---|
| 35 | B.10 | (dioxolane-(CH₂)₂—) | OH | mp. 138° C. |

TABLE F-2

| Co. No. | Ex. No. | —L | OR⁴ | Physical data |
|---|---|---|---|---|
| 36 | B.2 | $CH_3(CH_2)_3$— | OH | trans; mp. 80° C. |
| 37 | B.1 | $CH_3O(CH_2)_3$— | OH | trans; mp. 114° C. |
| 38 | B.6 | $CH_3$—CO—$(CH_2)_3$— | OH | trans; .$C_2H_2O_4$ (1:1); mp. 200° C. |
| 39 | B.1 | HO—$(CH_2)_3$— | OH | trans |
| 40 | B.1 | NC—$(CH_2)_3$— | OH | trans; mp. 120° C. |
| 41 | B.2 | $C_6H_5$—$CH_2$— | OH | trans; mp. 144° C. |
| 42 | B.1 | $C_6H_5$—CO—$CH_2$— | OH | trans; .$C_2H_2O_4$ (1:1); mp. 190° C. |
| 43 | B.1 | 4-F—$C_6H_5$—O—$(CH_2)_3$— | OH | trans; mp. 110° C. |
| 44 | B.1 | (2-methyl-1,3-dioxolan-2-yl)-(CH₂)₃— | OH | trans |
| 45 | B.1 | (2-methyl-1,3-dioxolan-2-yl)-(CH₂)₃— | OH | trans; .$C_2H_2O_4$ (1:1); mp. 148° C. |
| 46 | B.1 | (1-ethyl-3-(propyl)-benzimidazol-2(3H)-one)—(CH₂)₃— | OH | trans |
| 47 | B.1 | $CH_3$—$SO_2$—NH—$(CH_2)_2$— | OH | trans; .$C_2H_2O_4$ (1:1) |
| 48 | B.1 | (pyrrolidin-1-yl-C(=O))—$(CH_2)_3$— | OH | trans; .$C_2H_2O_4$ (1:1); mp. 138° C. |

TABLE F-2-continued

[Structure: L—N(piperidine with OR⁴)—CH₂—NH—C(=O)—(6-chloro-chroman-8-yl)]

| Co. No. | Ex. No. | —L | OR⁴ | Physical data |
|---|---|---|---|---|
| 49 | B.1 | (tetrahydrofuran-2-yl)-CH₂— | OH | trans |
| 50 | B.1 | (1,3-dioxolan-2-yl)-CH₂— | OH | trans; .H₂O (1:1); mp. 92° C. |
| 51 | B.10 | (1,3-dioxolan-2-yl)-(CH₂)₂— | OH | trans; mp. 114° C. |
| 52 | B.10 | HO—(CH₂)₂—O—(CH₂)₂— | OH | trans; .C₂H₂O₄ (1:1); mp. 158° C. |
| 53 | B.1 | CH₃—O—CO—(CH₂)₃— | OH | trans; mp. 80° C. |
| 54 | B.6 | HO—CO—(CH₂)₃— | OH | trans; .HCl (1:1); mp. 260° C. |
| 55 | B.1 | CH₃—O—CO—(CH₂)₄— | OH | trans; mp. 82° C. |
| 56 | B.11 | HO—(CH₂)₂— | OH | trans; .HCl (1:1), mp. 228° C. |
| 57 | B.1 | CH₃—O—CO—(CH₂)₂— | OH | Trans; mp. 160° C. |
| 58 | B.6 | HO—CO—(CH₂)₄— | OH | trans; .HCl (1:1), .H₂O (1:1); mp. 188° C. |
| 59 | B.3 | NC—(CH₂)₂— | OH | trans; mp. 160° C. |
| 60 | B.6 | HO—CO—(CH₂)₂— | OH | trans; .HCl (1:1); mp. 236° C. |
| 61 | B.1 | HO—(CH₂)₄— | OH | trans; mp. 116° C. |

TABLE F-2a

[Structure: L—N(piperidine with OR⁴ at 4-position)—CH₂—NH—C(=O)—(6-chloro-chroman-8-yl)]

| Co. No. | Ex. No. | —L | OR⁴ | Physical data |
|---|---|---|---|---|
| 62 | B.10 | (1,3-dioxolan-2-yl)-(CH₂)₂— | OH | mp. 114° C. |

TABLE F-3

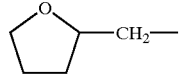

| Co. No. | Ex. No. | —L | OR⁴ | Physical data |
|---|---|---|---|---|
| 63 | B.2 | $CH_3(CH_2)_3-$ | OH | cis; $.C_2H_2O_4$ (1:1); mp. 162° C. |
| 64 | B.2 | $CH_3(CH_2)_3-$ | OH | trans |
| 65 | B.6 | $CH_3-CO-(CH_2)_3-$ | OH | trans |
| 66 | B.1 | $CH_3O(CH_2)_3-$ | OH | cis; $.C_2H_2O_4$ (1:1); mp. 160° C. |
| 67 | B.1 | $CH_3O(CH_2)_3-$ | OH | trans; mp. 110° C. |
| 68 | B.1 | $HO-(CH_2)_3-$ | OH | trans; mp. 120° C. |
| 69 | B.1 | 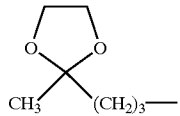 | OH | trans; mp. 80° C. |
| 70 | B.1 | 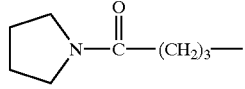 | OH | trans |
| 71 | B.1 | 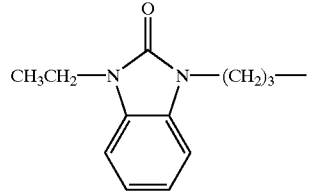 | OH | trans; mp. 80° C. |
| 72 | B.1 | $NC-CH_2-$ | OH | trans |
| 73 | B.3 | $NC-(CH_2)_2-$ | OH | trans |
| 74 | B.1 | $NC-(CH_2)_3-$ | OH | trans; $.C_2H_2O_4$ (1:1); mp. 198° C. |
| 75 | B.4 | $H_2N-(CH_2)_2-$ | OH | trans |
| 76 | B.4 | $H_2N-(CH_2)_3-$ | OH | trans |
| 77 | B.2 | $C_6H_5-CH_2-$ | OH | trans; mp. 176° C. |
| 78 | B.1 | $C_6H_5-CO-CH_2-$ | OH | trans; $.C_2H_2O_4$ (2:3); mp. 160° C. |
| 79 | B.1 | $4F-C_6H_4-O-(CH_2)_3-$ | OH | trans; $.H_2O$ (1:1); mp. 118° C. |
| 80 | B.1 | $4F-C_6H_4-O-(CH_2)_3-$ | OH | cis; $.C_2H_2O_4$ (1:1) |
| 81 | B.1 | 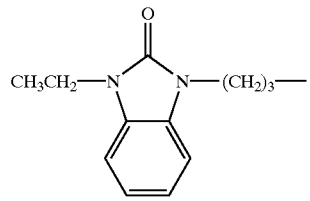 | OH | cis; $.C_2H_2O_4$ (1:2); mp. 130° C. |
| 82 | B.1 | 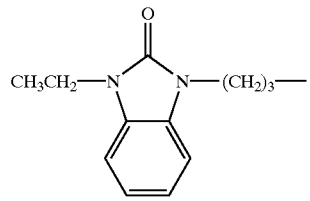 | OH | trans; $.H_2O$ (1:1); mp. 110° C. |
| 83 | B.5 | 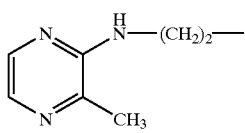 | OH | trans; mp. 152° C. |

TABLE F-3-continued

[Structure: L-N-piperidine with OR⁴ at 3-position, CH₂-NH-C(=O) linked to 7-chloro-2,3-dihydro-1,4-benzodioxine]

| Co. No. | Ex. No. | —L | OR⁴ | Physical data |
|---|---|---|---|---|
| 84 | B.5 | [3-methylpyrazin-2-yl-NH-(CH₂)₃—] | OH | trans |
| 85 | B.7 | [4-hydroxypyrimidin-2-yl-NH-(CH₂)₂—] | OH | trans; .H₂O (1:1) |
| 86 | B.2 | CH₃(CH₂)₃— | OCH₃ | cis; .C₂H₂O₄ (2:3); mp. 130° C. |
| 87 | B.1 | CH₃O(CH₂)₃— | OCH₃ | cis; .C₂H₂O₄ (1:1); mp. 170° C. |
| 88 | B.1 | 4F—C₆H₄—O—(CH₂)₃— | OCH₃ | cis; .C₂H₂O₄ (1:1); mp. 170° C. |
| 89 | B.2 | C₆H₅—CH₂— | OCH₃ | cis; mp. 155° C. |
| 90 | B.1 | [1,3-dioxolan-2-yl-CH₂—] | OH | trans; .H₂O (1:1); mp. 105° C. |
| 91 | B.10 | [1,3-dioxolan-2-yl-(CH₂)₂—] | OH | trans; .H₂O (1:1); mp. 94° C. |
| 92 | B.10 | HO—(CH₂)₂—O—(CH₂)₂— | OH | trans; .HCl (1:1); mp. 172–174° C. |
| 93 | B.1 | CH₃—O—CO—(CH₂)₃— | OH | trans; mp. 105° C. |
| 94 | B.6 | HO—CO—(CH₂)₃— | OH | trans; .HCl (1:1); mp. >100° C. |
| 95 | B.1 | CH₃—O—CO—(CH₂)₄— | OH | trans; .H₂O (1:1); mp. <60° C. |
| 96 | B.1 | CH₃—O—CO—(CH₂)₂— | OH | trans; mp. <80° C. |
| 97 | B.4 | NH₂—(CH₂)₃— | OH | trans; .C₂H₂O₄ (1:1) .C₃H₈O (1:1); mp. 88° C. |
| 98 | B.6 | HO—CO—(CH₂)₄— | OH | trans; .HCl (1:1) .H₂O (1:1); mp. >125° C. |
| 99 | B.6 | HO—CO—(CH₂)₂— | OH | trans; .HCl (1:1); mp. >210 |

TABLE F-3a

[Structure: L-N-piperidine with OR⁴ at 4-position and CH₂-NH-C(=O) also at 4-position, linked to 7-chloro-2,3-dihydro-1,4-benzodioxine]

| Co. No. | Ex. No. | —L | OR⁴ | Physical data |
|---|---|---|---|---|
| 100 | B.2 | CH₃(CH₂)₃— | OH | .HCl (1:1) .H₂O (1:1) |
| 101 | B.1 | CH₃O(CH₂)₃— | OH | .C₂H₂O₄ (1:1); mp. 186° C. |

TABLE F-3a-continued

| Co. No. | Ex. No. | —L | OR⁴ | Physical data |
|---|---|---|---|---|
| 102 | B.10 | (1,3-dioxolan-2-yl)-CH₂— | OH | mp. 137° C. |
| 103 | B.1 | CH₃—SO₂—(CH₂)₃— | OH | .H₂O (1:1); mp. 80° C. |
| 104 | B.1 | 2-methyl-1,3-dioxolan-2-yl-(CH₂)₃— | OH | mp. 100° C. |
| 105 | B.1 | 1-oxo-phthalazin-2-yl-(CH₂)₂— | OH | mp. 144° C. |
| 106 | B.6 | CH₃—CO—(CH₂)₃— | OH | .H₂O (1:1) |
| 107 | B.1 | HO—(CH₂)₂—O—(CH₂)₂ | OH | .(Z)-C₄H₄O₄: mp. 162° C. |
| 108 | B.1 | (tetrahydrofuran-2-yl)-CH₂— | OH | .C₂H₂O₄ (1:1) |
| 109 | B.1 | (7-methyl-5-oxo-5H-thiazolo[3,2-a]pyrimidin-6-yl)-(CH₂)₂— | OH | .H₂O (1:1); mp. 130° C. |
| 110 | B.1 | (tetrahydrofuran-2-yl)-(CH₂)₃— | OH | .C₂H₂O₄ (1:1); mp. 166° C. |
| 111 | B.1 | (tetrahydrofuran-2-yl)-(CH₂)₂— | OH | .C₂H₂O₄ (1:1) |
| 112 | B.1 | NC—CH₂— | OH | — |
| 113 | B.4 | H₂N—(CH₂)₂— | OH | — |
| 114 | B.7 | (4-hydroxypyrimidin-2-yl)-NH-(CH₂)₂— | OH | mp. 220° C. |
| 115 | B.5 | (3-methylpyrazin-2-yl)-NH-(CH₂)₂— | OH | mp. 174° C. |

TABLE F-3a-continued

[Structure: L-N-piperidine with OR⁴ and CH₂-NH-C(=O)- linked to chloro-benzodioxine]

| Co. No. | Ex. No. | —L | OR⁴ | Physical data |
|---|---|---|---|---|
| 116 | B.1 | (CH₃)₂CH-N(C=O)N(imidazolin-2-one)-(CH₂)₂— | OH | .C₂H₂O₄ (2:3); mp. 166° C. |
| 117 | B.1 | 1,3-dioxane-2-yl-(CH₂)₂— | OH | .H₂O (1:1); mp. 112° C. |
| 118 | B.10 | 1,3-dioxolan-2-yl-(CH₂)₂— | OH | .C₂H₂O₄ (1:1); mp. 196° C. |

TABLE F-4

[Structure: L-N-piperidine with OR⁴ and CH₂-NH-C(=O)- linked to chloro-benzodioxepine]

| Co. No. | Ex. No. | —L | OR⁴ | Physical data |
|---|---|---|---|---|
| 119 | B.2 | CH₃(CH₂)₃— | OH | trans; mp. 92° C. |
| 120 | B.2 | CH₃O(CH₂)₃— | OH | trans; mp. 84° C. |
| 121 | B.6 | CH₃CO(CH₂)₃— | OH | trans; .H₂O (1:1) |
| 122 | B.1 | tetrahydrofuran-2-yl-CH₂— | OH | trans |
| 123 | B.1 | tetrahydrofuran-2-yl-(CH₂)₂— | OH | trans; mp. 95° C. |
| 124 | B.1 | 2-methyl-1,3-dioxolan-2-yl-(CH₂)₃— | OH | trans |
| 125 | B.1 | 2-methyl-1,3-dioxolan-2-yl-(CH₂)₃— | OH | trans; .C₂H₂O₄ (1:1); mp. 176° C. |

TABLE F-4-continued

[Structure: piperidine with OR⁴ at 3-position, L on N, and CH₂-NH-C(=O)- linked to a chlorobenzene fused with a 7-membered dioxepane ring]

| Co. No. | Ex. No. | —L | OR⁴ | Physical data |
|---|---|---|---|---|
| 126 | B.1 | NC—(CH₂)₃— | OH | trans |
| 127 | B.2 | C₆H₅—CH₂— | OH | trans; mp. 140° C. |
| 128 | B.1 | HO—(CH₂)₂O(CH₂)₂— | OH | trans; mp. 106–107° C. |
| 129 | B.1 | CH₃O(CH₂)₃— | OCH₃ | cis; .C₂H₂O₄ (1:1); mp. 172–173° C. |
| 130 | B.2 | CH₃(CH₂)₃— | OCH₃ | cis; .C₂H₂O₄ (2:3) |
| 131 | B.2 | CH₃(CH₂)₃— | OCH₃ | trans; .C₂H₂O₄ (1:1); mp. 170° C. |
| 132 | B.2 | C₆H₅—CH₂— | OCH₃ | trans; mp. 90° C. |
| 133 | B.2 | C₆H₅—CH₂— | OCH₃ | cis; .C₂H₂O₄ (1:1) |
| 134 | B.1 | [2-methyl-1,3-dioxolan-2-yl]-(CH₂)₃— | OCH₃ | cis; .C₂H₂O₄ (1:1) |
| 135 | B.6 | CH₃CO(CH₂)₃— | OCH₃ | cis; .C₂H₂O₄ (1:1) |
| 136 | B.1 | [tetrahydrofuran-2-yl]-CH₂— | OCH₃ | trans; .C₂H₂O₄ (1:1) |
| 137 | B.1 | [2-methyl-1,3-dioxolan-2-yl]-(CH₂)₃— | OCH₃ | trans; .C₂H₂O₄ (1:1) |
| 138 | B.1 | CH₃O(CH₂)₃— | OCH₃ | trans; .C₂H₂O₄ (1:1) |
| 139 | B.6 | CH₃CO(CH₂)₃— | OCH₃ | trans; .C₂H₂O₄ (1:1); mp. 160° C. |
| 140 | B.1 | [tetrahydrofuran-2-yl]-CH₂— | OCH₃ | cis; .C₂H₂O₄ (1:1); mp. >60° C. |
| 141 | B.1 | [1,3-dioxolan-2-yl]-CH₂— | OH | trans; .H₂O (1:1); mp. 80° C. |
| 142 | B.10 | [1,3-dioxolan-2-yl]-(CH₂)₂— | OH | trans; .H₂O (1:1) |
| 143 | B.10 | [1,3-dioxolan-2-yl]-(CH₂)₂— | OH | trans |
| 144 | B.10 | HO—(CH₂)₃— | OH | trans |
| 145 | B.1 | CH₃—O—CO—(CH₂)₃— | OH | trans |
| 146 | B.6 | HO—CO—(CH₂)₃— | OH | trans; .HCl (1:1); mp. >170° C. |
| 147 | B.11 | HO—(CH₂)₂— | OH | trans; mp. 108° C. |
| 148 | B.1 | NC—CH₂— | OH | trans |
| 149 | B.4 | H₂N—(CH₂)₂— | OH | trans; mp. 148° C. |
| 150 | B.1 | CH₃—O—CO—(CH₂)₂— | OH | trans; .H₂O (1:1); mp. 80° C. |
| 151 | B.6 | HO—CO—(CH₂)₂— | OH | trans; .HCl (1:1); mp. 226° C. |
| 152 | B.1 | CH₃—O—CO—(CH₂)₄— | OH | trans; .H₂O (1:1); mp. 80–82° C. |
| 153 | B.1 | C₂H₅—O—CO—NH—(CH₂)₂— | OH | trans; .H₂O (1:1) |
| 154 | B.1 | CH₃—O—CO—(CH₂)₃— | OH | (3S-trans); .(E)-C₄H₄O₄ (1:1); |

TABLE F-4-continued

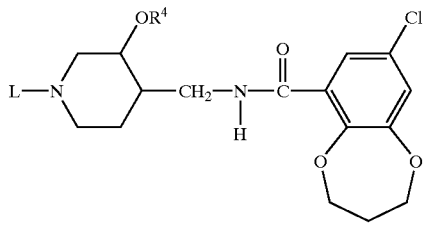

| Co. No. | Ex. No. | —L | OR⁴ | Physical data |
|---|---|---|---|---|
| 155 | B.1 | CH₃—O—CO—(CH₂)₃— | OH | mp. 145° C.; $[\alpha]_D^{20}$ = −9.76° (c = 25.10 mg/5 ml in CH₃OH) (3S-trans) |
| 156 | B.12 | HO—CO—(CH₂)₃— | OH | (3S-trans); .HCl.H₂O; mp. 145° C.; $[\alpha]_D^{20}$ = −12.64° (c. = 24.93 mg/5 ml in CH₃OH) |
| 157 | B.3 | NC—(CH₂)₂— | OH | trans |
| 158 | B.4 | H₂N—(CH₂)₃— | OH | trans |
| 159 | B.13 | C₂H₅—O—CO—NH—(CH₂)₃— | OH | trans; H₂O (1:1); mp. 70° C. |
| 160 | B.1 | HO—(CH₂)₃— | OH | trans; mp. 113° C. |
| 161 | B.4 | H₂N—(CH₂)₄— | OH | trans; H₂O (1:1); mp. 80–85° C. |
| 162 | B.6 | HO—CO—(CH₂)₄— | OH | trans; HCl (1:1); mp. 190° C. |
| 163 | B.13 | C₂H₅—O—CO—NH—(CH₂)₄— | OH | trans; C₂H₂O₄ (1:1); mp. 132–136° C. |
| 164 | B.1 | CH₃—O—CO—(CH₂)₃— | OH | (3R-trans); .(E)-C₄H₄O₄ (1:1); mp. 146° C.; $[\alpha]_D^{20}$ = +9.56° (c = 25.10 mg/5 ml in CH₃OH) |
| 165 | B.12 | HO—CO—(CH₂)₃— | OH | (3R-trans); .HCl (1:1); mp. >125° C.; $[\alpha]_D^{20}$ = +12.61° (c = 25.37 mg/5 ml in CH₃OH) |

TABLE F-4a

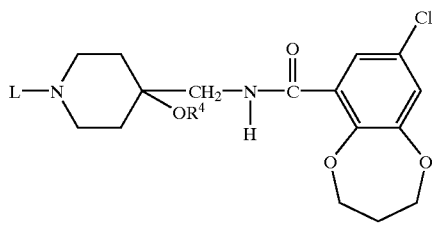

| Co. No. | Ex. No. | —L | OR⁴ | Physical data |
|---|---|---|---|---|
| 166 | B.1 | 1,3-dioxolan-2-yl—CH₂— | OH | .C₂H₂O₄ (1:1); mp. 186° C. |
| 167 | B.1 | NC—(CH₂)₃— | OH | .C₂H₂O₄ (1:1); mp. 134–138° C. |
| 168 | B.1 | CH₃—O—(CH₂)₃— | OH | .C₂H₂O₄ (1:1); mp. 148° C. |
| 169 | B.1 | CH₃—SO₂—(CH₂)₃— | OH | .H₂O (1:1); mp. 76–80° C. |
| 170 | B.1 | tetrahydrofuran-2-yl—(CH₂)₂— | OH | .C₂H₂O₄ (1:1) |
| 171 | B.2 | CH₃—(CH₂)₃— | OH | .C₂H₂O₄ (1:1); mp. 156° C. |
| 172 | B.1 | tetrahydrofuran-2-yl—(CH₂)₃— | OH | .C₂H₂O₄ (1:1); mp. 148° C. |

TABLE F-4a-continued

[Structure: L-N-piperidine with CH2-N(H)-C(=O) linker to 8-chloro-benzodioxepine; piperidine bears OR4]

| Co. No. | Ex. No. | —L | OR4 | Physical data |
|---|---|---|---|---|
| 173 | B.1 | [6-(CH2)2-substituted 7-methyl-5H-thiazolo[3,2-a]pyrimidin-5-one] | OH | .C2H2O4 (1:1) .H2O (1:1); mp. 154° C. |
| 174 | B.1 | [2-(CH2)2-substituted phthalazin-1(2H)-one] | OH | mp. 148° C. |
| 175 | B.1 | NC—CH2— | OH | — |
| 176 | B.4 | H2N—(CH2)2— | OH | — |
| 177 | B.7 | [4-hydroxy-2-(NH(CH2)2—)pyrimidine] | OH | mp. 196° C. |
| 178 | B.1 | [2-(CH2)2-substituted 1,3-dioxolane] | OH | mp. 82° C. |
| 179 | B.1 | [2-methyl-2-(CH2)3-substituted 1,3-dioxolane] | OH | — |
| 180 | B.6 | CH3CO(CH2)3— | OH | .H2O (1:1); mp. 75–77° C. |
| 181 | B.5 | [3-methyl-2-(NH(CH2)2—)pyrazine] | OH | .C2H2O4 (1:2); mp. 170° C. |

TABLE F-5

| Co. No. | Ex. No. | —L | OR⁴ | Physical data |
|---|---|---|---|---|
| 182 | B.2 | $CH_3(CH_2)_3-$ | OH | trans; .H$_2$O (1:1); mp. 90° C. |
| 183 | B.1 | $CH_3O-(CH_2)_3-$ | OH | trans; mp. ±68° C. |
| 184 | B.6 | $CH_3-CO-(CH_2)_3-$ | OH | trans; .C$_2$H$_2$O$_4$ (1:1); mp. 169° C. |
| 185 | B.1 | (tetrahydrofuran-2-yl)-CH$_2$— | OH | trans; .H$_2$O (1:1); mp. 80° C. |
| 186 | B.1 | (tetrahydrofuran-2-yl)-(CH$_2$)$_2$— | OH | trans; mp. ±108° C. |
| 187 | B.1 | 2-methyl-1,3-dioxolan-2-yl-(CH$_2$)$_3$— | OH | trans; mp. 83–84° C. |
| 188 | B.1 | $NC-(CH_2)_3-$ | OH | trans; .C$_2$H$_2$O$_4$ (1:1); mp. ±120° C. |
| 189 | B.2 | $C_6H_5-CH_2-$ | OH | trans |
| 190 | B.1 | $HO-(CH_2)_2O(CH_2)_2-$ | OH | trans; mp. 128° C. |
| 191 | B.1 | (1,3-dioxolan-2-yl)-CH$_2$— | OH | trans; .H$_2$O (1:1); mp. 90° C. |
| 192 | B.10 | $HO-(CH_2)_3-$ | OH | trans |
| 193 | B.1 | $CH_3-O-CO-(CH_2)_3-$ | OH | trans |
| 194 | B.6 | $HO-CO-(CH_2)_3-$ | OH | trans; .HCl (1:1); mp. 90° C. |
| 195 | B.1 | $CH_3-O-CO-(CH_2)_2-$ | OH | trans; .H$_2$O (1:1); mp. >60° C. |
| 196 | B.11 | $HO-(CH_2)_2-$ | OH | trans; mp. 116–117° C. |
| 197 | B.3 | $NC-(CH_2)_2-$ | OH | trans; mp. 105–107° C. |
| 198 | B.12 | $HO-CO-(CH_2)_2-$ | OH | trans; .HCl (1:1); mp. >185° C. |

TABLE F-5a

| Co. No. | Ex. No. | —L | OR⁴ | Physical data |
|---|---|---|---|---|
| 199 | B.10 | (tetrahydrofuran-2-yl)-(CH$_2$)$_2$— | OH | — |

Pharmacological examples

Example C.1: "5HT$_4$ antagonism in rat oesophageal tunica muscularis mucosae"

The 5HT$_4$ antagonistic potence of the present compounds was measured as described in Baxter G.S. et. al, Naunyn-Schmiedeberg's Arch. Pharmacol., 343, 439–446 (191).

The pA$_2$ value is calculated as follows:

$$pA_2 = \log \frac{\text{concentration test compound (mol/l)}}{\text{agonist concentration ratio} - 1}$$

TABLE C.1

5HT$_4$ antagonistic data

| Co. No. | pA$_2$ |
|---|---|
| 1 | 8.53 |
| 2 | 10.5 |
| 3 | 8.07 |
| 4 | — |
| 5 | — |
| 6 | — |

TABLE C.1-continued
5HT$_4$ antagonistic data
| Co. No. | pA$_2$ |
|---|---|
| 7 | — |
| 8 | 9.7 |
| 9 | — |
| 10 | — |
| 11 | 8.76 |
| 12 | 10.2 |
| 13 | 8.35 |
| 14 | 9.2 |
| 15 | 8.4 |
| 16 | 9.6 |
| 17 | 9.6 |
| 21 | <8 |
| 24 | 9.3 |
| 26 | 8.8 |
| 28 | — |
| 29 | 9.6 |
| 30 | 9.6 |
| 31 | 9.4 |
| 32 | <8 |
| 35 | 9 |
| 36 | 9.8 |
| 37 | — |
| 38 | — |
| 39 | 9.81 |
| 40 | — |
| 41 | 9.7 |
| 42 | 9.5 |
| 43 | 9.8 |
| 45 | — |
| 46 | 9.52 |
| 47 | — |
| 48 | 9.67 |
| 49 | 10.35 |
| 50 | 9.3 |
| 51 | 10 |
| 52 | 9.5 |
| 53 | 9.5 |
| 54 | 9.8 |
| 62 | 9 |
| 63 | 9.49 |
| 64 | 10.00 |
| 65 | 9.44 |
| 66 | 9.26 |
| 67 | 9.43 |
| 68 | 9.04 |
| 69 | 9.11 |
| 71 | 9.13 |
| 74 | 9.22 |
| 77 | 9.19 |
| 78 | 8.44 |
| 79 | 7.93 |
| 80 | 8.83 |
| 81 | 8.47 |
| 82 | 9.79 |
| 83 | 10.29 |
| 84 | 10.55 |
| 85 | 9.52 |
| 86 | 8.2 |
| 87 | 8.46 |
| 88 | 9.2 |
| 89 | <8 |
| 90 | 9.4 |
| 91 | 10 |
| 92 | 9.7 |
| 93 | 9.4 |
| 94 | 9.24 |
| 100 | <8 |
| 101 | <7 |
| 102 | — |
| 103 | <8 |
| 104 | <8 |
| 105 | ~8 |
| 106 | <8 |
| 107 | <8 |
| 108 | 8.4 |
| 109 | <8 |
| 110 | ~8 |
| 111 | 8.5 |
| 114 | ~8 |
| 115 | 8.3 |
| 116 | ~8 |
| 117 | <8 |
| 118 | ~8 |
| 119 | 10.65 |
| 120 | 9.72 |
| 121 | 9.9 |
| 122 | 9.81 |
| 123 | 9.95 |
| 125 | 10.2 |
| 126 | 9.78 |
| 127 | — |
| 128 | — |
| 129 | >8 |
| 130 | 8.5 |
| 131 | 9.5 |
| 132 | 8.5 |
| 134 | 8.4 |
| 135 | 8.1 |
| 139 | 8.6 |
| 141 | 9.6 |
| 142 | 10.2 |
| 143 | 10.2 |
| 144 | 10.4 |
| 146 | 9.1 |
| 166 | 8.6 |
| 167 | <8 |
| 168 | <8 |
| 169 | <8 |
| 170 | 8.3 |
| 171 | <8 |
| 172 | 8.5 |
| 173 | ~8 |
| 174 | <8 |
| 177 | ~8 |
| 178 | ~8 |
| 179 | ~8 |
| 180 | ~7.5 |
| 181 | <8 |
| 182 | 9.4 |
| 183 | — |
| 184 | — |
| 185 | 10.2 |
| 186 | 9.34 |
| 187 | 9.5 |
| 188 | 10.5 |
| 189 | — |
| 190 | 8.3 |
| 191 | 8.6 |
| 192 | 10.1 |
| 194 | 9 |
What is claimed is:
1. A compound of formula (I)
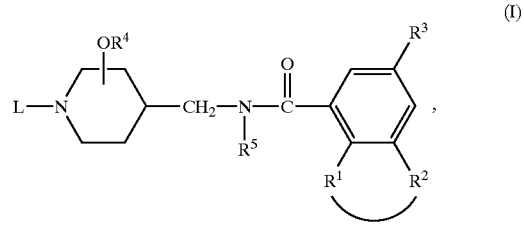
a stereochemically isomeric form thereof, an N-oxide form thereof, or a pharmaceutically acceptable acid or base addition salt thereof, wherein —R$^1$—R$^2$— is a bivalent radical of formula —O—CH₂—O—,  (a-1)

—O—CH₂—CH₂—,  (a-2)

—O—CH₂—CH₂—O—,  (a-3)

—O—CH₂—CH₂—CH₂—,  (a-4)

—O—CH₂—CH₂—CH₂—O—,  (a-5)

—O—CH₂—CH₂—CH₂—CH₂—,  (a-6)

—O—CH₂—CH₂—CH₂—CH₂—O—,  (a-7)

—O—CH₂—CH₂—CH₂—CH₂—CH₂—,  (a-8)

wherein in said bivalent radicals optionally one or two hydrogen atoms on the same or a different carbon atom may be replaced by $C_{1-6}$alkyl or hydroxy, $R^3$ is hydrogen or halo;
$R^4$ is hydrogen or $C_{1-6}$alkyl;
$R^5$ is hydrogen or $C_{1-6}$alkyl;
L is $C_{3-6}$cycloalkyl, oxo$C_{5-6}$cycloalkyl, or $C_{2-6}$alkenyl, or L is a radical of formula —Alk—$R^6$,  (b-1)

—Alk—X—$R^7$,  (b-2)

—Alk—Y—C(=O)—$R^9$, or  (b-3)

—Alk—Y—C(=O)—$NR^{11}R^{12}$,  (b-4)

wherein each Alk is $C_{1-12}$alkanediyl; and
$R^6$ is hydrogen, cyano, amino, $C_{1-6}$alkylsulfonylamino, $C_{3-6}$cycloalkyl, oxo$C_{5-6}$cycloalkyl, aryl or Het¹;
$R^7$ is hydrogen, $C_{1-6}$alkyl, hydroxy$C_{1-6}$alkyl, $C_{3-6}$cycloalkyl, aryl or Het²;
X is O, S, SO₂ or $NR^8$; said $R^8$ being hydrogen or $C_{1-6}$alkyl;
$R^9$ is hydrogen, $C_{16}$alkyl, $C_{3-6}$cycloalkyl, $C_{1-6}$alkyloxy, hydroxy or aryl; Y is a direct bond, $NR^{10}$, O, S, O—(CH2)$_n$—, S—(CH₂)$_n$—, or —$NR^{10}$—(CH₂)$_n$—, wherein n is an integer from 1 to 6, and $R^{10}$ being hydrogen or $C_{1-6}$alkyl;
$R^{11}$ and $R^{12}$ each independently are hydrogen, $C_{1-6}$alkyl, $C_{3-6}$cycloalkyl, or $R^{11}$ and $R^{12}$ combined with the nitrogen atom bearing $R^{11}$ and $R^{12}$ may form a pyrrolidinyl or piperidinyl ring both being optionally substituted with $C_{1-6}$alkyl, amino or mono or di($C_{1-6}$alkyl)amino, or said $R^{11}$ and $R^{12}$ combined with the nitrogen bearing $R^{11}$ and $R^{12}$ may form a piperazinyl or 4-morpholinyl radical both being optionally substituted with $C_{1-6}$alkyl; and
each aryl represents unsubstituted phenyl or phenyl substituted with 1, 2 or 3 substituents each independently selected from halo, hydroxy, $C_{1-6}$alkyl, $C_{1-6}$alkyloxy, amino-sulfonyl, $C_{1-6}$alkylcarbonyl, nitro, trifluoromethyl, amino or aminocarbonyl; and
Het¹ and Het² each independently are selected from furan; furan substituted with $C_{1-6}$alkyl or halo; tetrahydrofuran; tetrahydrofuran substituted with $C_{1-6}$alkyl; dioxolane; dioxolane substituted with $C_{1-6}$alkyl; dioxane; dioxane substituted with $C_{1-6}$alkyl; tetrahydropyran; tetrahydropyran substituted with $C_{1-6}$alkyl; pyrrolidinyl; pyrrolidinyl substituted with one or two substituents each independently selected from halo, hydroxy, cyano, or $C_{1-6}$alkyl; pyridinyl; pyridinyl substituted with one or two substituents each independently selected from halo, hydroxy, cyano, $C_{1-6}$alkyl; pyrimidinyl; pyrimidinyl substituted with one or two substituents each independently selected from halo, hydroxy, cyano, $C_{1-6}$alkyl, $C_{1-6}$alkyloxy, amino and mono and di($C_{1-6}$ alkyl)amino; pyridazinyl; pyridazinyl substituted with one or two substituents each independently selected from hydroxy, $C_{1-6}$alkyloxy, $C_{1-6}$alkyl or halo; pyrazinyl; pyrazinyl substituted with one ore two substituents each independently selected from halo, hydroxy, cyano, $C_{1-6}$alkyl, $C_{1-6}$alkyloxy, amino, mono- and di($C_{1-6}$alkyl)amino and $C_{1-6}$alkyloxycarbonyl;

Het¹ can also be a radical of formula

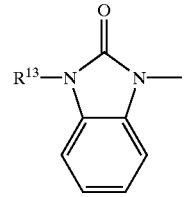
(c-1)

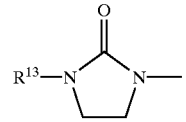
(c-2)

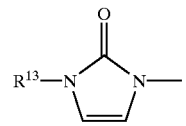
(c-3)

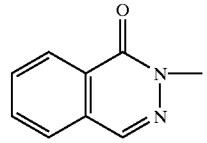
(c-4)

Het¹ and Het² each independently can also be selected from the radicals of formula

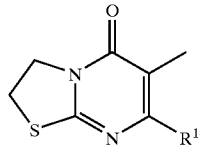
(d-1)

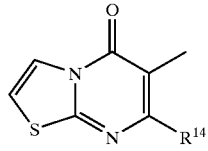
(d-2)

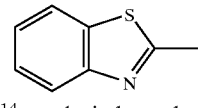
(d-3)

$R^{13}$ and $R^{14}$ each independently are hydrogen or $C_{1-4}$alkyl.

2. A compound as claimed in claim 1 wherein the —$OR^4$ radical is situated at the 3-position of the piperidine moiety having the trans configuration.

3. A compound as claimed in claim 1 wherein the —$OR^4$ radical is situated at the 4-position of the piperidine moiety.

4. A compound as claimed in claim 1 wherein the compound is:

(3S-trans)-4-[[[(8-chloro-3,4-dihydro-2H-1,5-benzodioxepin-6-yl)carbonyl]amino]methyl]-3-hydroxy-1-piperidinebutanoic acid, a pharmaceutically acceptable acid addition salt or an N-oxide thereof.

5. A pharmaceutical composition comprising a pharmaceutically acceptable carrier and a therapeutically active amount of a compound according to claim 1.

6. A process for preparing a pharmaceutical composition wherein a therapeutically active amount of a compound according to claim 1 is intimately mixed with a pharmaceutically acceptable carrier.

7. A process for preparing a compound of formula (I) wherein
a) an intermediate of formula (II) is N-alkylated with an intermediate of formula (III) in a reaction-inert solvent and, optionally in the presence of a suitable base,

L—W +
(II)

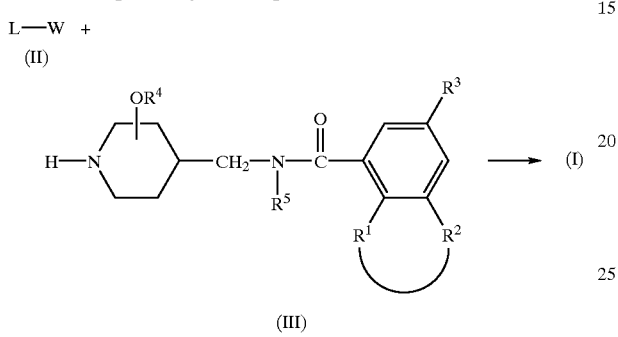

(III)

b) an appropriate ketone or aldehyde intermediate of formula L'=O (IV), said L'=O being a compound of formula L-H, wherein two geminal hydrogen atoms in the $C_{1-12}$alkanediyl moiety are replaced by =O, is reacted with an intermediate of formula (III);

L=O +
(IV)

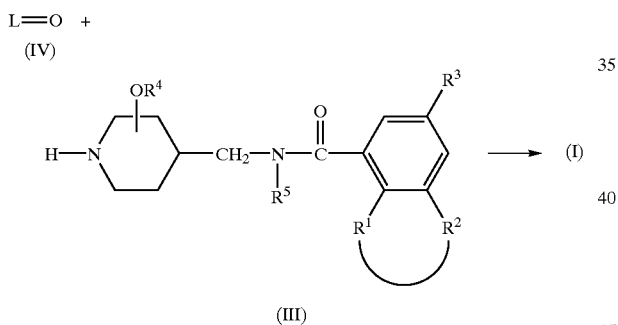

(III)

c) an intermediate of formula (V) is reacted with an carboxylic acid derivative of formula (VI) or a reactive functional derivative thereof;

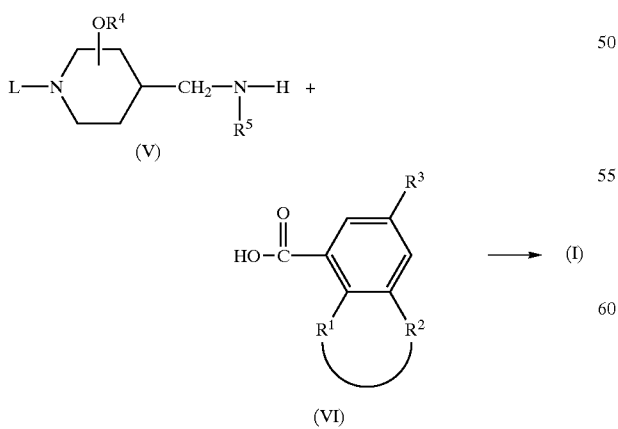

(VI)

d) an intermediate of formula (VII), wherein X is bromo or iodo, is carbonylated in the presence of an intermediate of formula (V) in a reaction-inert solvent in the presence of a suitable catalyst and a tertiary amine, and at a temperature ranging between room temperature and the reflux temperature of the reaction mixture;

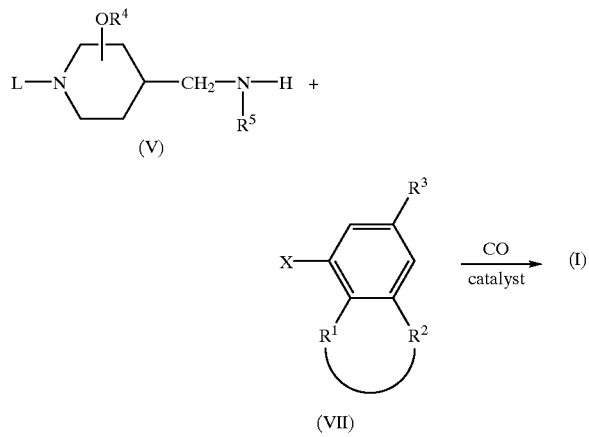

wherein in the above reaction schemes the radicals L, $R^1$, $R^2$, $R^3$, $R^4$ and $R^5$ are as defined in claim 1 and W is an appropriate leaving group;

e) or, compounds of formula (I) are converted into each other following art-known transformation reactions; or if desired; a compound of formula (I) is converted into a pharmaceutically acceptable acid addition salt, or conversely, an acid addition salt of a compound of formula (I) is converted into a free base form with alkali; and, if desired, preparing stereochemically isomeric forms thereof.

8. A method for treating hypermotility, irritable bowel syndrome (IBS), constipation-predominant IBS, diarrhea-predominant IBS, pain-predominant IBS, non-pain-predominant IBS, bowel hypersensitivity and the reduction of pain associated with gastrointestinal hypersensitivity and/or hyperactivity comprising administering an effective amount of a compound according to claim 1.

9. A compound of formula (III)

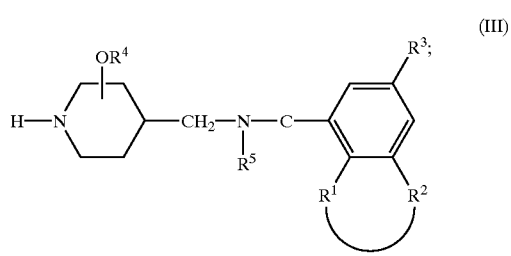

a pharmaceutically acceptable acid addition salt thereof or a stereochemically isomeric form thereof, wherein $R^1$, $R^2$, $R^3$, $R^4$ and $R^5$ are as defined in claim 1.

* * * * *